United States Patent [19]
Saeki et al.

[11] Patent Number: 5,125,821
[45] Date of Patent: Jun. 30, 1992

[54] RESIN FLOW AND CURING MEASURING DEVICE

[75] Inventors: Junichi Saeki; Isamu Yoshida; Aizo Kaneda; Kazuhiro Sugino, all of Yokohama; Kunihiko Nishi, Kokubunji, all of Japan

[73] Assignee: Hitachi, Ltd., Tokyo, Japan

[21] Appl. No.: 429,471

[22] Filed: Oct. 31, 1989

[30] Foreign Application Priority Data

Oct. 31, 1988 [JP] Japan .................. 63-272965
Oct. 31, 1988 [JP] Japan .................. 63-272966

[51] Int. Cl.⁵ .................. B29C 45/76; B29C 47/92; G01N 11/04
[52] U.S. Cl. .................. 425/170; 73/54.09; 264/40.1; 425/149; 425/171; 425/544
[58] Field of Search .......... 425/145, 149, 150, 543, 425/544, 135, 169, 170, 171, DIG. 228; 264/40.1, 40.3, 40.5; 73/54, 56, 64.1

[56] References Cited

U.S. PATENT DOCUMENTS

| | | | |
|---|---|---|---|
| 3,033,021 | 5/1962 | Dickason | 73/56 |
| 3,579,799 | 5/1971 | Furstenberg | 249/59 |
| 4,240,996 | 12/1980 | Hunkar | 425/149 |
| 4,241,602 | 12/1980 | Han et al. | 73/56 |
| 4,678,420 | 7/1987 | Inoue | 425/149 |
| 4,743,190 | 5/1988 | Brunnschweiler et al. | 425/149 |
| 4,774,675 | 9/1988 | Kagawa | 425/149 |
| 4,850,217 | 7/1989 | Nunn | 73/56 |
| 4,875,363 | 10/1989 | Hinduja et al. | 73/56 |

FOREIGN PATENT DOCUMENTS

| | | | |
|---|---|---|---|
| 1080511 | 9/1957 | France | 73/56 |
| 89/04243 | 5/1989 | PCT Int'l Appl. | 73/56 |
| 444968 | 12/1974 | U.S.S.R. | 73/56 |

OTHER PUBLICATIONS

Saeki et al, "Simulation of Balanced Filling in a Multi-Cavity Mold for Encapsulation of Semiconductor Devices", 4th Annual International Polymer Processing Society Meeting, May 1988.

Primary Examiner—Jay H. Woo
Assistant Examiner—James P. Mackey
Attorney, Agent, or Firm—Antonelli, Terry, Stout & Kraus

[57] ABSTRACT

A measuring device for enabling an evaluation of a moldability of a thermosetting resin by determination of parameters suitable for high accuracy forecasting of flow and curing behaviors of the thermosetting resin within a metal mold, as well as a metal mold for molding a thermosetting resin and method for constructing runners of the metal mold which is effective to minimize if not prevent the occurrence of false in moldings. By utilizing unique or peculiar parameters of the thermosetting resin which are not influenced by a molding condition and by conducting a flow simulation with a metal mold having a flow passage of arbitrary dimensions using the determined values for the parameters, a forecasting of a flow in an actual metal mold is enabled so as to preselect optimum molding conditions and flow passage dimensions for a metal mold.

13 Claims, 27 Drawing Sheets

A-A

B-B

RESIN FLOW AND CURING MEASURING DEVICE

BACKGROUND OF THE INVENTION

The present invention relates to a measuring device and method and, more particularly, to a measuring device and method for enabling an evaluation of a moldability of a thermosetting resin by determination of parameters suitable for high accuracy forecasting of flow and curing behaviors of a resin within a metal mold, as well as a metal mold for molding a thermosetting resin and method for constructing runners of the metal mold which is effective to minimize if not prevent the occurrence of faults in moldings.

In, for example, Japanese patent laid open no. 59-88656, an apparatus is proposed wherein an average apparent viscosity in a predetermined section in a flow passage of a metal mold is actually measured.

In accordance with the above proposed arrangement, apparent flow and curing characteristic values in given conditions of dimensions of a flow passage of a metal mold and given molding conditions are determined; however, a forecasting of a flow in a metal mold having a flow passage of differing dimensions cannot be accomplished because the proposed arrangement is incapable of determining parameters peculiar to a resin which is not influenced by such conditions.

Moreover, as a practical problem, providing or constructing a metal mold having a flow passage which has the nearest possible dimensions to dimensions of a metal mold capable of being mass produced results in high production costs for the metal mold.

In, for example, Japanese publication no. 55-17697, a method of designing runners of a metal mold having a plurality of mold cavities for molding a thermosetting is proposed wherein a runner of the molten thermosetting resin is formed so that the depth of the runner decreases gradually toward an extremity thereof, with a restriction angle of a gate for a mold cavity furthest from a mold receiving pot being greater than that of a gate for a mold cavity nearer to the mold receiving pot whereby a sum of pressure losses in the runner and gate is the same for all mold cavities.

A disadvantage of the last proposed method resides in the fact that the method disregards the estimating of a flow mode of the resin which flows through a runner having a complicated shape while the temperature and viscosity of the resin vary. Consequently, it is extremely difficult to charge all of the mold cavities of the metal mold at equal charging rates. Therefore, any possible improvement in the quality of the products molded in a metal mold produced in accordance with this proposed method is extremely limited.

In a paper entitled "Simulation of Balanced Filling in a Multi-Cavity Mold for Encapsulation of Semiconductor Device", J. Saeki and A. Kaneda, Processing Society Meeting, May 8-11, 1988, a method for analyzing mold filling dynamics through a channel of circular cross-section is proposed which examines viscosity and enables a quick and accurate evaluation of rheological properties of commercial molding components by a data measuring and analyzing apparatus.

A disadvantage of the last mentioned method and apparatus resides in the fact that the proposed data measuring and analyzing apparatus does not take into account various parameters unique to particular thermosetting resins and, consequently, the proposed techniques do not permit an optimization of a metal mold construction which is readily reproducible and ensures production of fault free molds.

In, for example, an article entitled "Simulation of Balanced Filling in a Multi-Cavity Mold for Encapsulation of Semiconductor Device", Nikkei Microdevices, vol. 6, 1988, pps. 95-102, a transfer molding method and apparatus is proposed which decreases the costs and necessary developing for producing a plastic molded package for an LSI.

While the technique proposed in the last mentioned publication can reduce void defects in a mold to about one-third and reduce distortion of a gold lead to about one-fifth of other conventional proposals, the proposed techniques are ineffective since such techniques do not take into consideration non-isothermal viscosity behavior of a thermosetting resin nor take into account unique or peculiar parameters of a particular resin. Consequently, the last mentioned proposal does not provide a total solution to optimize the quality of the products molded in a metal mold since the proposal does not recognize nor utilize unique flow and curing parameters of particular thermosetting resins being employed in the molding process.

SUMMARY OF THE INVENTION

The aim underlying the present invention essentially resides in providing a measuring apparatus for determining flow and curing parameters unique or peculiar to a molding resin with a high degree of accuracy as well as a metal mold and method of designing or constructing a runner of a metal mold using the flow and curve characteristics of the molding resin.

In accordance with advantageous features of the present invention, changes in the viscosity under several metal mold temperature conditions using several metal molds having flow passage which have uniform sectional dimensions along a flow direction of the resin are actually measured, by an automatic measuring device, where the pressure loss, flow distance, flow rate, average apparent viscosity, etc., of the molding resin and the flow passages are calculated and outputted and evaluated so as to determine optimum constructional features or characteristics of a metal mold.

Moreover, according to the present invention, values of parameters are estimated in isothermal viscosity equations for flow simulation from characteristic values of the thermosetting resin by an extrapolation method, with the values being inputted and a flow simulation being conducted under the same conditions as experimentally carried out. The actual measured values and the calculated values of change in viscosity are compared with each other and the values of the parameters are successively corrected, with the values of the parameters being determined when the corrected values of the parameters come into a predetermined range of error.

By virtue of the measuring device and method of the present invention, values of parameters unique or peculiar to a molding resin which are not influenced by molding conditions can be determined with a high degree of accuracy, and, by conducting a flow simulation with a metal mold having a flow passage of arbitrary dimensions using the values of the parameters, a forecasting of the flow in an actual metal mold is possible, with a selection of optimal molding conditions and metal mold flow passage dimensions being readily determined in advance so as to facilitate a designing of a metal mold in a minimal amount of time and at a substantial reduction in cost.

In accordance with still further features of the present invention, an estimation of the flow of a thermosetting resin within a metal mold is accomplished by dividing the runner of the metal mold into a plurality of sections, calculating specific form resistance $\beta$ and flow rate Q for each section of the runner, and simulating the flow of the thermosetting resin in each section of the runner on an assumption that a shape of the section of the runner is cylindrical. The temperature, viscosity, flow speed, and mean apparent viscosity $\bar{\eta}a$ of the molding resin in each section is calculated and a pressure loss is determined on the basis of the relationship $\Delta P = \beta \cdot \bar{\eta}a \cdot Q$.

In accordance with the method of the present invention, it is possible to strictly determine the specific form resistance and flow rate of a runner to calculate pressure loss necessary for an optimum runner design. Moreover, since the runner of a practical or actual metal mold normally requiring a complicated flow analysis and a considerable analysis time can be obtained by analyzing a combination of cylindrical passages, and the mean apparent viscosity in each cylindrical passage is calculated in the present invention, a flow analysis can be completed with a very short calculating time and the pressure loss can be estimated with a sufficiently high accuracy.

Additionally, by virtue of the novel features of the present invention, it is possible to remarkably reduce the time necessary for the development of a product as well as to improve the quality of the product by determining optimum dimensions of a metal mold and molding conditions through quick and highly accurate simulation of the mold of flow of a molding resin within the metal mold.

In accordance with the present invention, a device for measuring flow in curing characteristics of a resin is provided which includes a metal mold having a pot and a flow passage connected to the pot, with a plunger for injecting resin supplied to the pot into a flow passage. A resin pressure detector is provided in the metal mold, with a displacement detector being provided for detecting a position of the plunger. Data processing means are provided for storing and arranging signals from the resin pressure detector and the displacement detector, with a calculating means executing a physical quantity conversion of the processed signals and a calculation in combination of a physical quantity and constant calculated from various dimensions of flow passages of the metal mold. An outputting means is provided for enabling an outputting of a result of the calculation from the calculating means.

For the purposes of measuring the flow and curing characteristics of a thermosetting resin, in accordance with the present invention, the metal mold is provided with a single runner connecting the pot and a single flow passage connected to an end of the runner at an end opposite of the pot. The single flow passage is provided with cross-sectional dimensions with a uniform along a flow direction of the resin, and the sectional area of the flow passage is less than the sectional area of the runner. Advantageously, the cross-sectional shape of the flow passage of the metal mold is a circle, with a shape of the flow passage of the metal mold in a flow direction of the thermosetting resin being helical or spiral.

Advantageously, the pressure detector means is mounted on a wall of the runner of the metal mold, and the metal mold is constructed so that the flow passage section is capable of being separated from the runner section.

In order to determine or judge when the thermosetting resin begins to flow into the flow passage and to terminate a measurement of the flow, according to the present invention, two pressure levels for comparative purposes are provided with a signal of the pressure detector being set. Upon exceeding the first pressure level, it is determined that the thermosetting resin has begun to flow and, upon exceeding the second pressure level, the flow measurement is terminated.

According to the present invention, a difference between adjacent signals of the displacement detector is calculated and, when such difference is lower than a predetermined level and the signal of the pressure detector exceeds the preset second pressure level, the measurement of the flow of the thermosetting resin is ended.

In accordance with still further features of the present invention, a changing rate of pressure data relative to time is retroactively determined from a point of time at which the measurement of the flow of the thermosetting resin is ended or terminated, and the point of time at which the value of the changing rate becomes smaller than a predetermined value is regarded as a flow stopping point of time.

To estimate a pressure loss within a metal mold in order to obtain data for designing or constructing a metallic mold having a pot and runner extending from the pot, in accordance with the present invention, a volume of the runners is calculated on the basis of predetermined dimensions of the runner, with a thermosetting resin injecting time being set in which a plunger injects the thermosetting resin introduced into the pot into the runners. The flow rate of the thermosetting resin injected into the runners is calculated, and the flow rate is divided by the number of branches formed by the runners. The flow rate of the thermosetting resin is calculated at an optional position in the runner, and the runner is divided into a plurality of sections by planes extending perpendicular to a flow direction of the thermosetting resin. A form resistance of the runner for each section of the runner is calculated on the basis of a width, depth, cross-sectional shape and length of the runner, and each section of the runner is simulated by an equivalent cylindrical passage. Basic equations expressing a variable-viscosity transportation phenomenon of the thermosetting resin in each cylindrical passage are solved by utilizing initial and boundary conditions, and the temperature, viscosity, flow velocity, and mean apparent viscosity of the resin in each cylindrical passage is calculated. A calculating pressure loss in each section is determined in accordance with a relationship of the form resistance, mean apparent viscosity, and flow rate of the thermosetting resin at the optional position in the runner, and the pressure losses for all of the sections of the runner are summed up or totalled to obtain an overall pressure loss.

According to the present invention, the calculated overall pressure loss is compared with a predetermined reference pressure loss and the overall pressure loss as calculated by changing a value of at least one of dimensions of the runner, injection time, temperature of the metal mold, and resin preheating temperature when the predetermined reference pressure loss is less than or equal to the calculated overall pressure loss, with the conditions being sequentially varied until values of the dimensions of the runner and molding conditions satisfy an inequality wherein the predetermined pressure reference loss is greater than the calculated overall pressure loss.

The dimensions of the runner and molding conditions according to the present invention are determined so that the predetermined reference pressure loss is greater than the calculated overall pressure loss, and the viscosity of the thermosetting resin before a predetermined radial position is not greater than the viscosity after the predetermined radial position.

With a metal mold having a pot, a runner extending from the pot, and a plurality of mold cavities arranged along the runner and respectively communicating with the runner by gate means, the number of joining planes of the sections corresponds at least to the number of branches branching from the runner, with the dimensions of the gate means for each mold cavity being determined in accordance with the present invention so that the sum of pressure losses in the runner and the gate means is the same for all mold cavities in order that the flow rate is equally distributed to all of the mold cavities.

A circular or spiral pipe flow passage connected to the runner in accordance with the present invention has a smaller cross-sectional area than the cross-sectional area of the runner, with the pressure detector detecting the pressure of the resin which flows into the circular or spiral pipe flow passage from the runner. The data processing means which inputs a signal from the pressure detector and the plunger displacement detector calculates an average apparent viscosity on the basis of predetermined values of the mold and the signals from the displacement and the pressure detector.

In constructing the runner of a mold utilizing the unique or peculiar flow and curing characteristics of the particular resin, according to the present invention, the resin material values unique or peculiar to flow and curing characteristics of the thermosetting resin, molding conditions, and dimensions of the mold are obtained. The runners are divided into a plurality of sections and a specific form resistance for each section and flow rate in the sections of the runner is calculated. Each section of the runner is substituted by a cylindrical passage and a pressure loss and viscosity at each section is calculated on the basis of an isothermal viscosity relationship, a non-isothermal viscosity relationship, a continuant relationship, as well as a relationship of momentum and conservation of energy. A pressure loss in the runner and viscosity are compared with a predetermined value, and a dimension of the mold on the basis of such comparison is determined.

The above and other objects, features, and advantages of the present invention will become more apparent from the following description when taken in connection with the accompanying drawings which show, for the purpose of illustration only, several embodiments in accordance with the present invention.

DETAILED DESCRIPTION

Figure 1A:
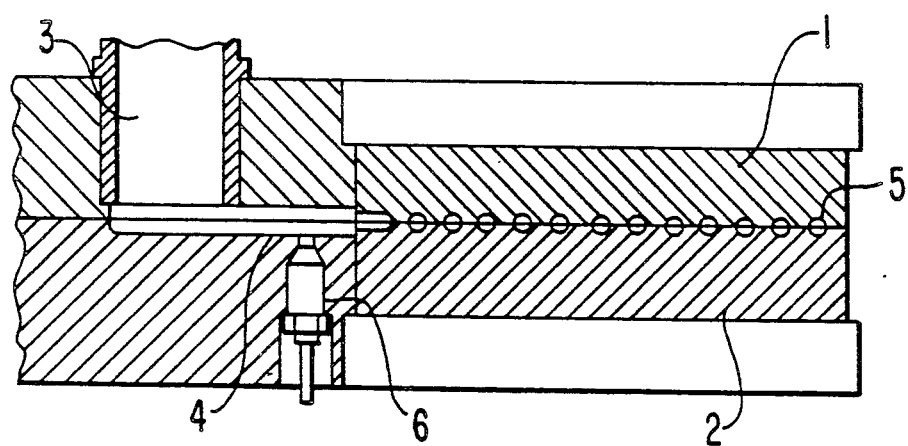
FIG. 1A is a vertical cross-sectional partial view of a metal mold constructed in accordance with the present invention.
Figure 1B:
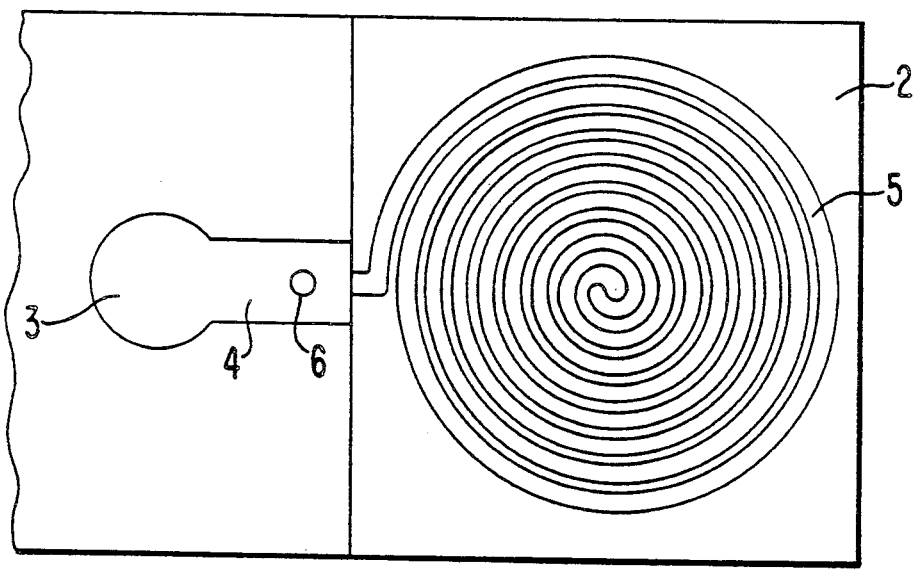
FIG. 1B is a partial top plan view of a female portion of the metal mold of FIG. 1A.

Referring now to the drawings wherein like reference numerals are used throughout the various views to designate like parts and, more particularly, to FIGS. 1A and 1B, according to these figures, a metal mold generally designated by the reference character M includes a male mold 1 and a female mold 2, with the male mold 1 including a pot 3 for receiving molding resin (not shown). The molding resin from the pot 3 passes through a runner 4 having a large cross-sectional area and flows into a spiral circular pipe flow passage 5. The metal mold M enables a determination in a change in viscosity of the molding resin within the circular pipe flow passage 5 and is constructed such that a loss in pressure is measured by a pressure detector 6, of a conventional construction, mounted on a wall of the runner 4.

The cross-sectional area of the runner 4 is greater than a cross-sectional area of the circular pipe flow passage 5 in order to reduce a thermal history or heat the molding resin absorbs from the metal mold 1 up to an isothermal condition until the molding resin enters the circular pipe flow passage 5, and in order to reduce a loss of the pressure in the runner 4 to enable a measurement of a point of time at which the flow of the molding resin in the circular pipe flow passage 5 begins, as well as a loss of pressure during a flow of the molding resin in the circular pipe flow passage 5 by the pressure detector 6 detecting a sudden rise in the pressure at the instant when an end of flow of the molding resin enters the circular pipe flow passage 5 having a smaller cross-sectional area. To enable a selection of an arbitrary circular flow passage 5, the metal mold M includes removable mold blocks receivable in the male and female molds 1, 2 for forming the circular pipe flow passage 5.

Table 1 provides an exemplary listing of sectional areas of circular flow passages 5 for the purposes of discussing the subject matter of the present invention; however, as can readily be appreciated, the diameters listed for the circular pipe flow passage 5 are merely examples and other diameters D can also be considered.

TABLE 1

| Flow Passage No. | Diameter D (mm) | Whole Length L (mm) |
|---|---|---|
| 1 | 2.0 | 4,850 |
| 2 | 4.0 | 3,300 |
| 3 | 6.0 | 2,570 |

The sectional areas listed in Table 1 were selected since such areas have substantially proximate values to those of flow passages of metal molds which may be employed at an encapsulating step for electronic components. The runner 4 of FIGS. 1A and 1B has a sectional area of about ten times a sectional area of flow passage No. 3 in Table 1. It is noted that, in accordance with the present invention, the molding resin used is an epoxy molding material for application to encapsulation of electronic parts, and the molding resin material will not flow to a terminal end of the circular pipe flow passage 5 but will stop flowing at a portion intermediate of the end of the circular spiral flow passage 5 due to a curing reaction.

Figure 2:
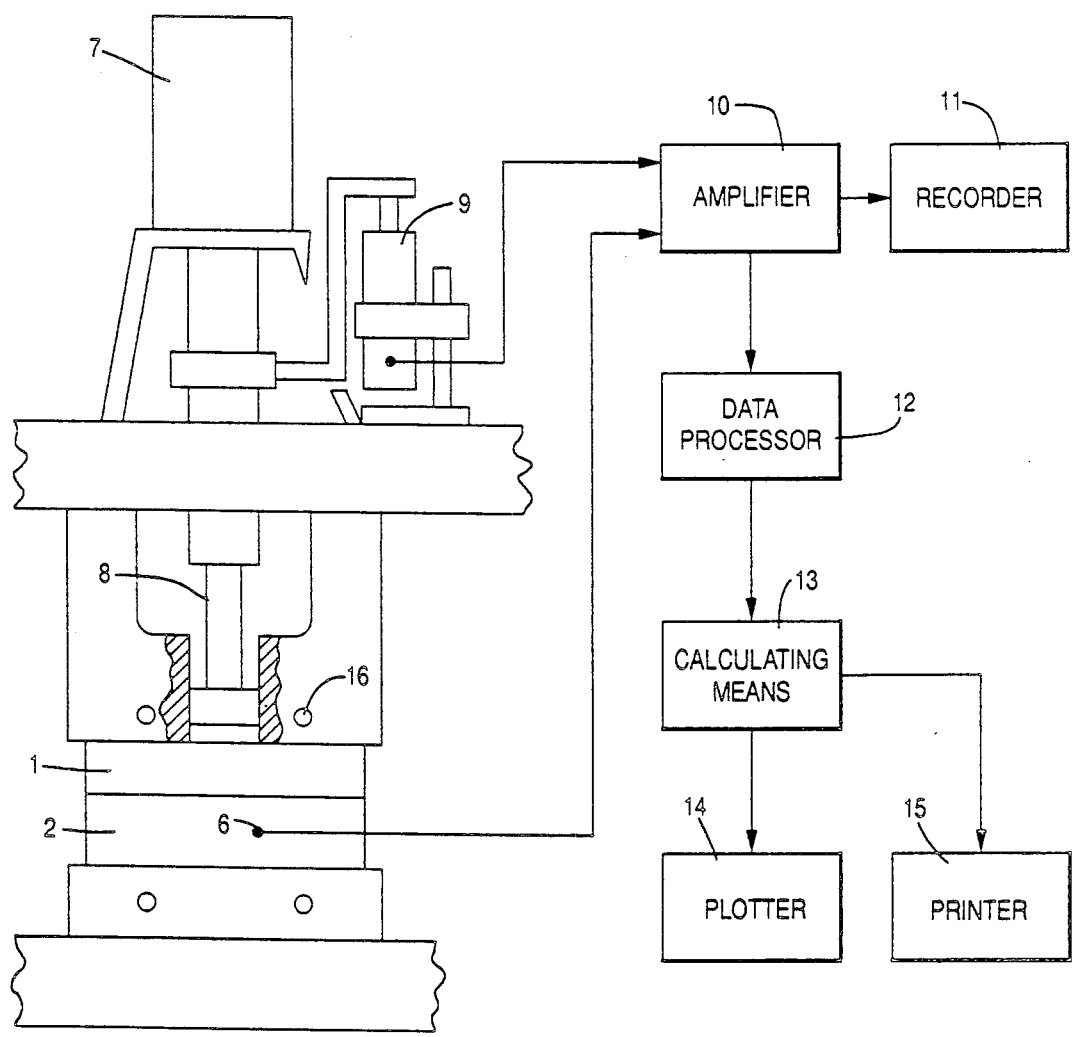
FIG. 2 is a schematic view of a transfer molding machine and control therefor constructed in accordance with the present invention.

As shown in FIG. 2, a transfer molding machine 7 includes a reciprocal plunger 8 adapted to be moved in a downward direction to feed molding resin material into the metal mold M. A displacement of the plunger 8 is detected by a conventional displacement detector 9 mounted on the molding machine 6, with an output signal indicative of the displacement of the plunger 8 being supplied to a conventional recorder means 11 and a conventional data processing means 12 by an amplifier means 10. An output signal of the pressure detected by the pressure detector 6, mounted on, for example, a wall of a runner of the female mold 2, is also supplied to the recorder means 11 and data processing means 12 by the amplifier means 10. The data processing means 12 includes a controlling microcomputer and various modules in combination and is adapted to execute storing and data arraying processes in a conventional manner.

Data processed by the data processing means 12 are subsequently transmitted or supplied to a conventional calculating means 13 in which calculations for physical quantity conversion of signals and calculations of characteristic values are executed. Finally, an output signal from the calculating means 13 is supplied to a plotter means 14 and/or printer means 15 so as to enable the results of the detection of the displacement of the plunger 8 by the detector 9 and detection of pressure by the pressure detector 6.

Figure 3:
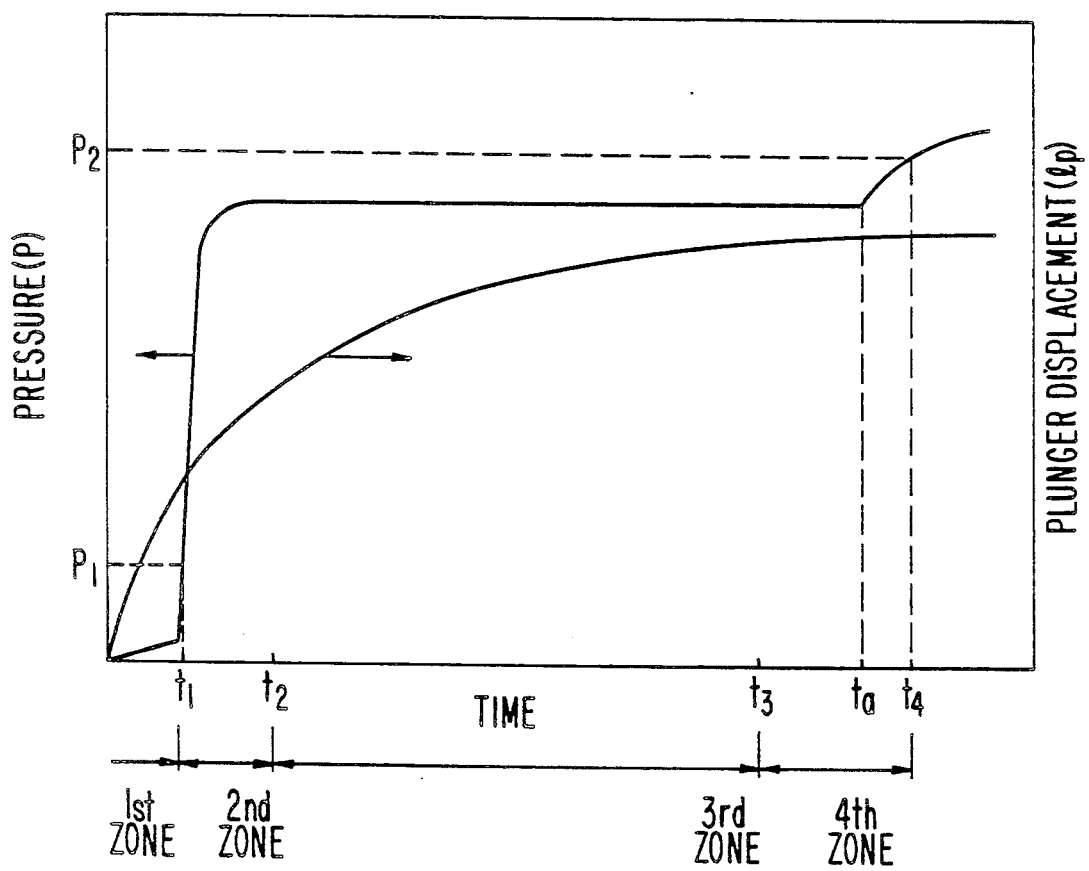
FIG. 3 is a graphical illustration of data determined in dependence upon values indicated by a recorder of a measuring device of the present invention.

FIG. 3 provides a graphical example of values indicated or provided by the recorder mean 11 when the molding resin material is caused to flow in the metal mold M. In FIG. 3, the reference character $t_1$ denotes a point of time at which a leading end of the flow of molding resin enters the circular pipe flow passage 5, and the sudden rise in the pressure P detected by the pressure detector 6 in a short period of time before and after the point of time $t_1$. After the point of time $t_1$, the pressure P exhibits a substantially fixed value and, after another point in time $t_a$ at which the flow of molding resin is stopped, a pressure rise resulting from a thermal expansion component once again takes place. Meanwhile, the change of the displacement $l_p$ of the plunger 8 has a tendency to decrease as the time passes.

More particularly, intervals of time for sampling of data were changed for individual zones such that the interval was short where the change in pressure was increased but the interval was long where the change in pressure was small. In FIG. 3, the 1st zone is provided to discriminate a point of time $t_1$ at which a leading end of the flow of the molding resin reaches the circular pipe flow passage 5, and a point of time after a preset pressure $P_1$ was exceeded was regarded as a point of time at which a flow of the molding resin in the circular pipe flow passage 5 was commenced. Meanwhile in the 2nd zone, a sampling is performed to a preset point in time $t_2$ in a region wherein the pressure change is still great. In the 3rd zone, sampling in a fixed pressure region to a point in time $t_3$ is carried out. The 4th zone is provided to enable a making of a judgment of a point of time $t_4$ at which the flow of the molding resin is stopped and in order to complete the measurement with certainty. The measurement was ended at the point of time $t_4$ when the two requirements were simultaneously met, namely, that the difference between adjacent data of the displacement $l_p$ of the plunger 8 is smaller or less than a predetermined value and the pressure is higher than a preset pressure $P_2$.

Figure 4:
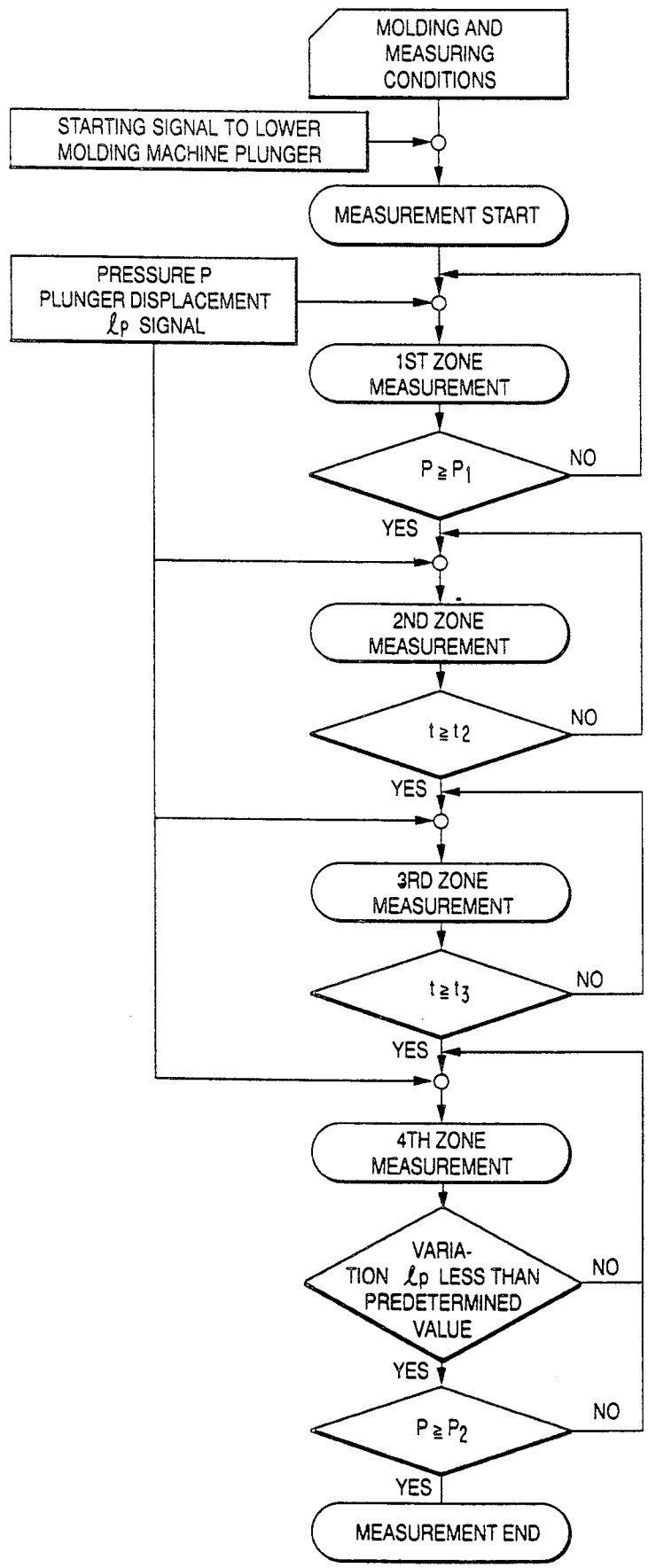
FIG. 4 is a flow chart for automatic data fetching.

FIG. 4 provides a flow chart for determining a measurement end. As shown in FIG. 4, automatic discrimination of the point of time $t_a$ proceeds such that, making use of a difference between a pressure changing ratio during the flow of the molding resin and a pressure changing ratio after a stopping of the flow of the molding resin, changing ratios may be successfully determined by linear approximation from adjacent data retroactively from the point of time at which the measurement was ended, and a point of time when the changing ratio was smaller than a predetermined value was regarded as the point of time $t_a$.

Figure 5:
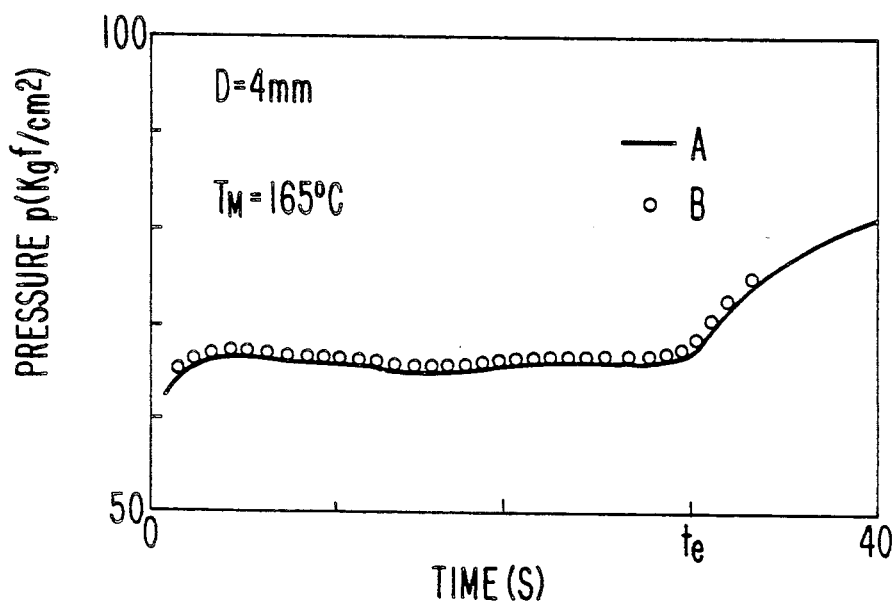
FIG. 5 is a graphical illustration of pressure data.

In FIG. 5, values of the pressure P were automatic measurements and calculations were executed by the above-described method are shown at B, with A representing values indicated by the recorder means 11. As apparent from FIG. 5, the automatic measurements and calculations of the values represented by A and B possess a very high conformity. In FIG. 5, the origin of time and $t_e$ coincide with $t_1$ and $t_a$ in FIG. 3, respectively, with $t_e$ being defined as an apparent gelation time. In FIG. 5, the diameter of the circular pipe passageway 5 was 4 mm, and the individual temperature $t_m$ of the metal mold was 165° C.

Figure 6:
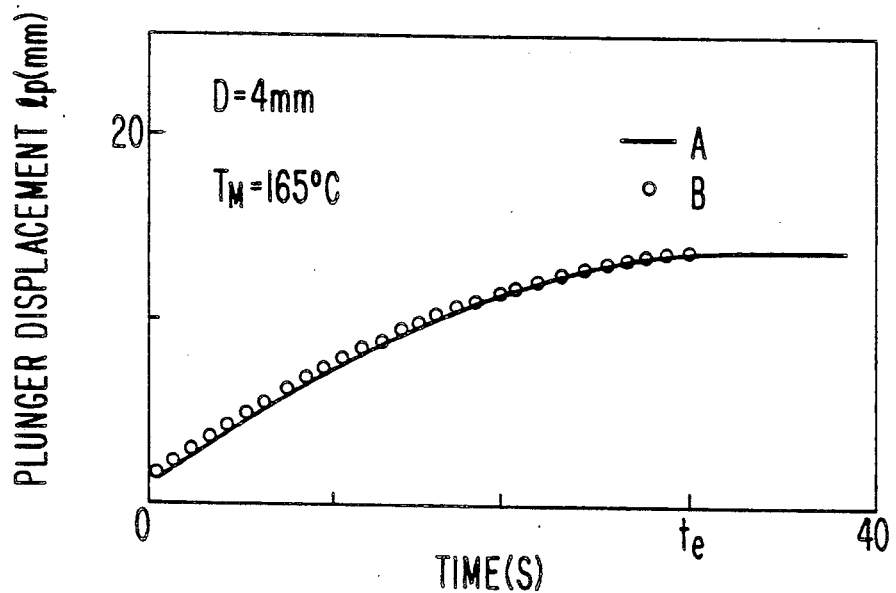
FIG. 6 is a graphical illustration of injection plunger displacement data.

Results of automatic measurements and calculations of the displacements $l_p$ of the plunger 8 experimentally determined under the same conditions as FIG. 5 are represented in FIG. 6 by the reference character B, with the reference character A representing values indicated by the recorder means 11. As apparent from FIG. 6, the values represented by the reference characters A and B display a very high conformity, with the values or data B representing values after execution of a processing graduation of data by a higher degree polynomial approximation method by the calculating means 13 in order to remove noises from the same. In FIG. 6, again the diameter D of the circular pipe passageway 5 was 4 mm and the individual temperature TM of the metal mold was 165° C.

Figure 7:
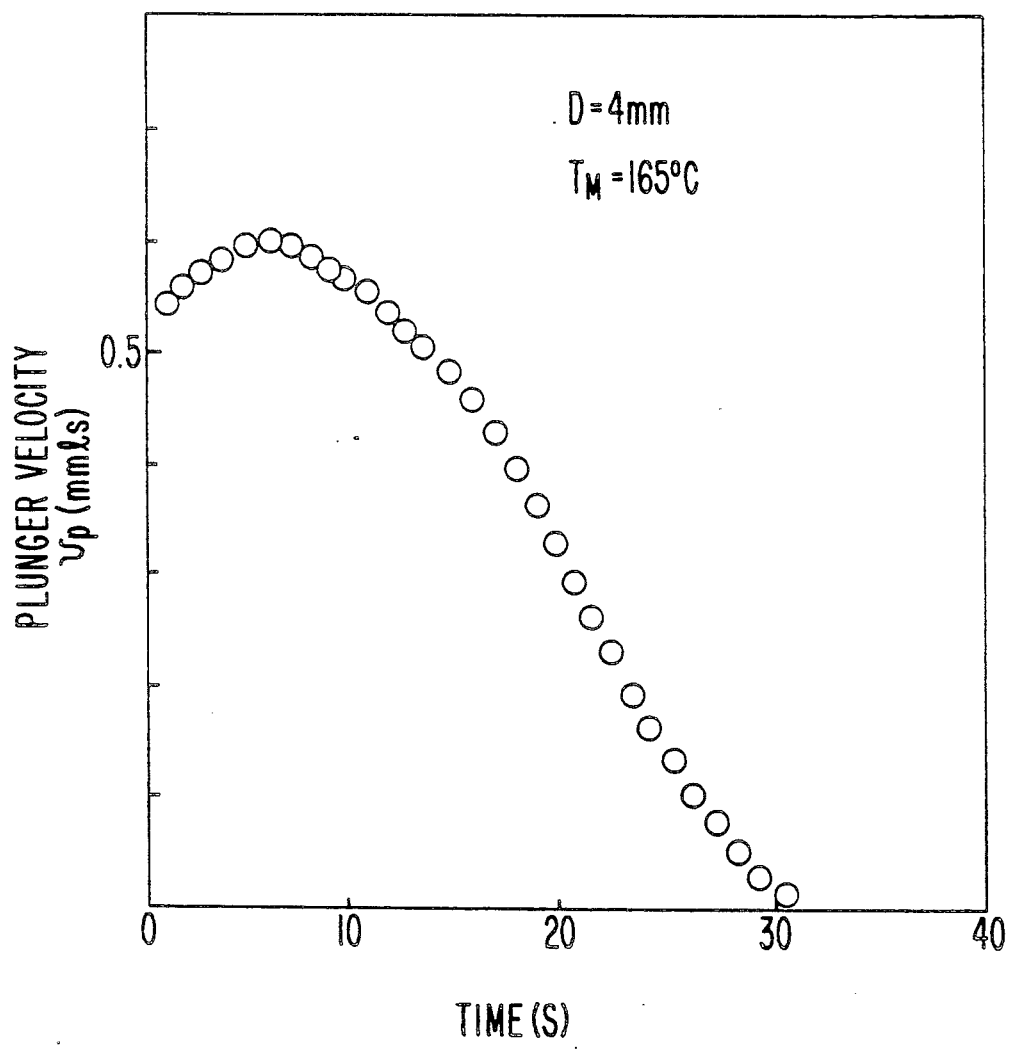
FIG. 7 is a graphical illustration of injection plunger velocity data.

The calculating means 13 is adapted to calculate a primary derivative of a determined polynomial of higher degree and then determine a lowering speed $v_P$ of the plunger 8 at a arbitrary point of time from the thus calculated primary derivative, with the results of time calculation being graphically depicted in FIG. 7. A velocity curve which is moderate with respect to time was obtained, with a viscosity of the molding resin being determined in accordance with the following equation:

$$\overline{\eta}_a = \frac{(D/2)^4 \Delta P}{8Ql} \quad (1)$$

where:

$\overline{\eta}a$ = an average apparent viscosity;
D = a diameter of the circular pipe flow passage 5;
$\Delta P$ = a pressure loss;
Q = a flow rate; and
l = a flow distance.

The diameter D of the circular pipe flow passage 5 is set in advance with the pressure loss $\Delta p$ being determined from the values of the pressure detected by the pressure detector 6, and the flow rate Q and flow distance l determined from a value indicated by the plunger displacement detector 9 and a ratio between sectional areas of the pot 3 and circular pipe flow passage 5 shown in FIGS. 6 and 7. Accordingly, a value for $\overline{\eta}a$ at an arbitrary point of time can be calculated from equation (1), with the necessary calculation being executed by the calculating means 13, and values of $\Delta P$, Q, l, $\overline{\eta}a$ and so on are drawn out and outputted after each preset interval of time to the plotter means 14 and printer means 15, respectively.

FIGS. 8–13 provide a graphical comparison of characteristic values determined in accordance with the present invention under the following conditions: the three types of circular pipe flow passages 5 of Table 1 were used; the temperatures $T_m$ of the metal mold M were 145° C., 165° C. and 185° C. respectively; and the molding resin was in the form of a tablet preliminarily heated to 75° C. by a high frequency heater (not shown) and then supplied into the pot 3 in order to enable a carrying out of the measurements.

Figure 8:
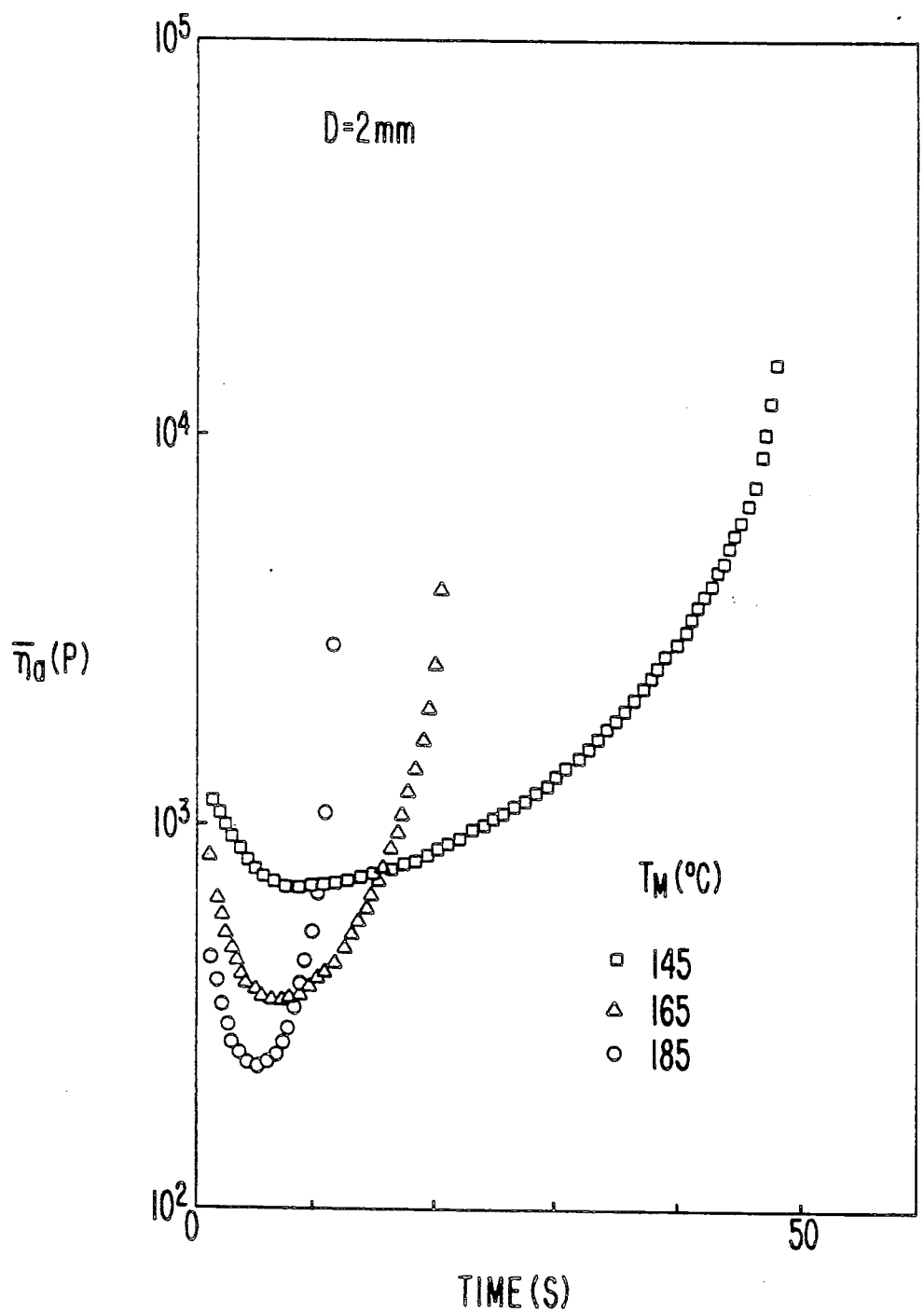
FIGS. 8–10 are graphical illustrations of changes of an average apparent viscosity with various pipe diameters.

FIG. 8 illustrates a relationship between the average apparent viscosity $\overline{\eta}a$ and the time at the individual temperatures $T_m$, with the circular pipe flow passage 5 having a pipe diameter D equal to 2 mm (Table 1, flow passage No. 1). At any individual temperature TM, the average apparent viscosity $\overline{\eta}a$ decreases as time passes and then continues to increase from a midpoint from a flow of the molding resin. This is because the molding resin temperature is increased by a transmission of heat from the walls of the circular pipe low passage 5 and a melting reaction and a curing reaction of the molding resin proceed at the same time, but a contribution of the heat from the walls prevails until the midpoint of the flow of molding resin and, thereafter, the melting and curing reaction are effective. If, for example, the minimum value of the average apparent viscosity $\overline{\eta}a$ is defined as an average apparent viscosity $\overline{\eta}b$, then as the individual temperature $T_M$ increases, the average apparent viscosity $\overline{\eta}b$ decreases. Meanwhile, the last data of the individual conditions are data immediately before the apparent gelation time $t_e$, and as the individual temperature $T_M$ increases, the flow time of the molding resin decreases. These conditions mean that, as the amount of heat transmitted from the metal mold M to the molding resin increases, the melting action and the curing action of the molding resin suddenly takes place in the same manner.

Figure 9:
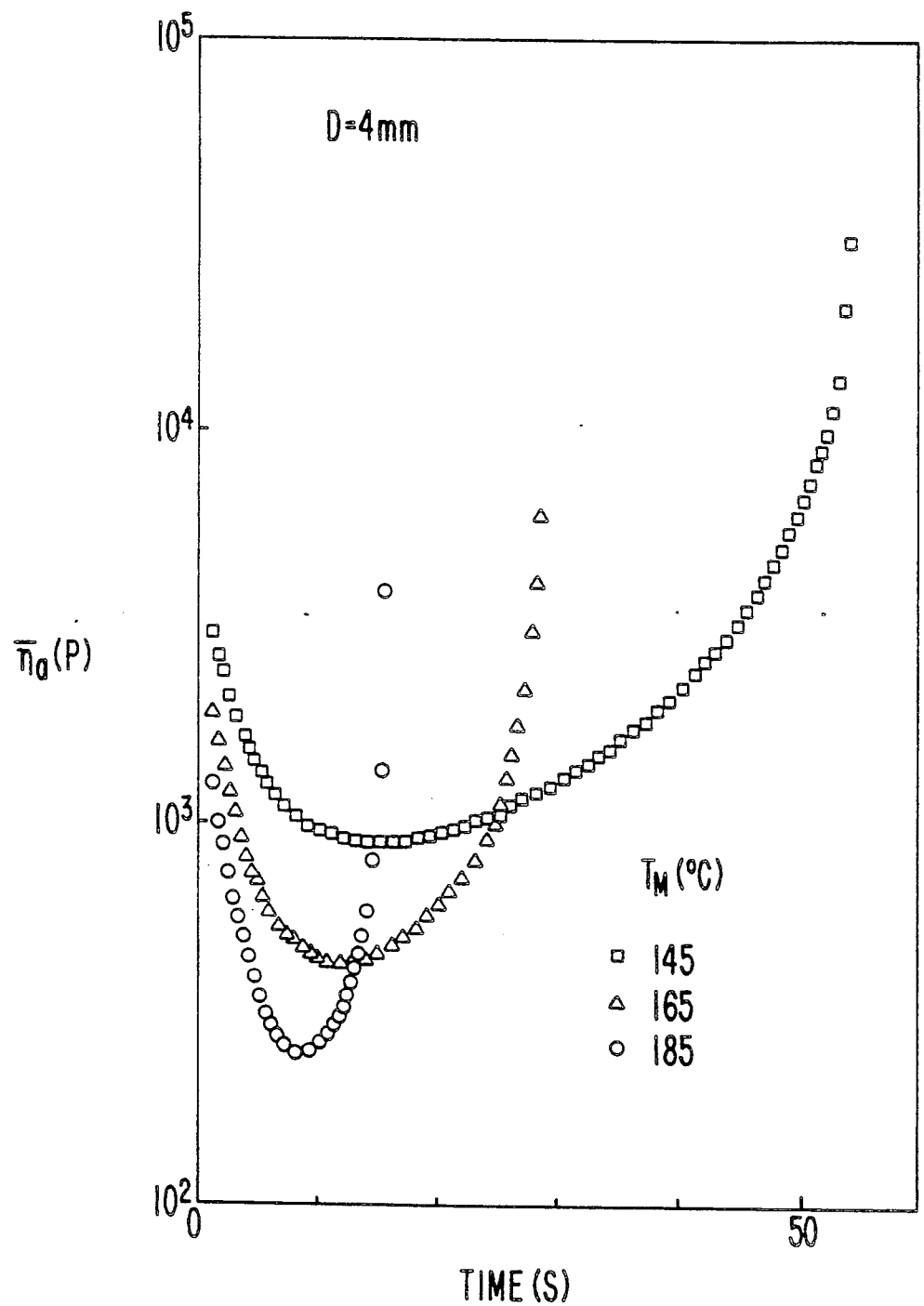

FIG. 9 graphically depicts the changes of the average apparent viscosity $\overline{\eta}a$ at the individual temperatures $T_m$ where the circular flow passage has a pipe diameter D equal to 4 mm (Table 1, flow passage no. 2). While the tendency of the changes in the apparent viscosity $\overline{\eta}a$ in FIG. 9 are similar to the changes of the apparent viscosity $\overline{\eta}a$ in FIG. 8, with a pipe diameter D equal to 2 mm, the flow time is greater and the value of the apparent average viscosity $\overline{\eta}b$ is higher at the same individual temperature $T_M$ due to an increase in size of the pipe diameter D of the circular pipe flow , transmission of the heat to the resin proceeds more slowly and melting and curing takes place more slowly.

Figure 10:
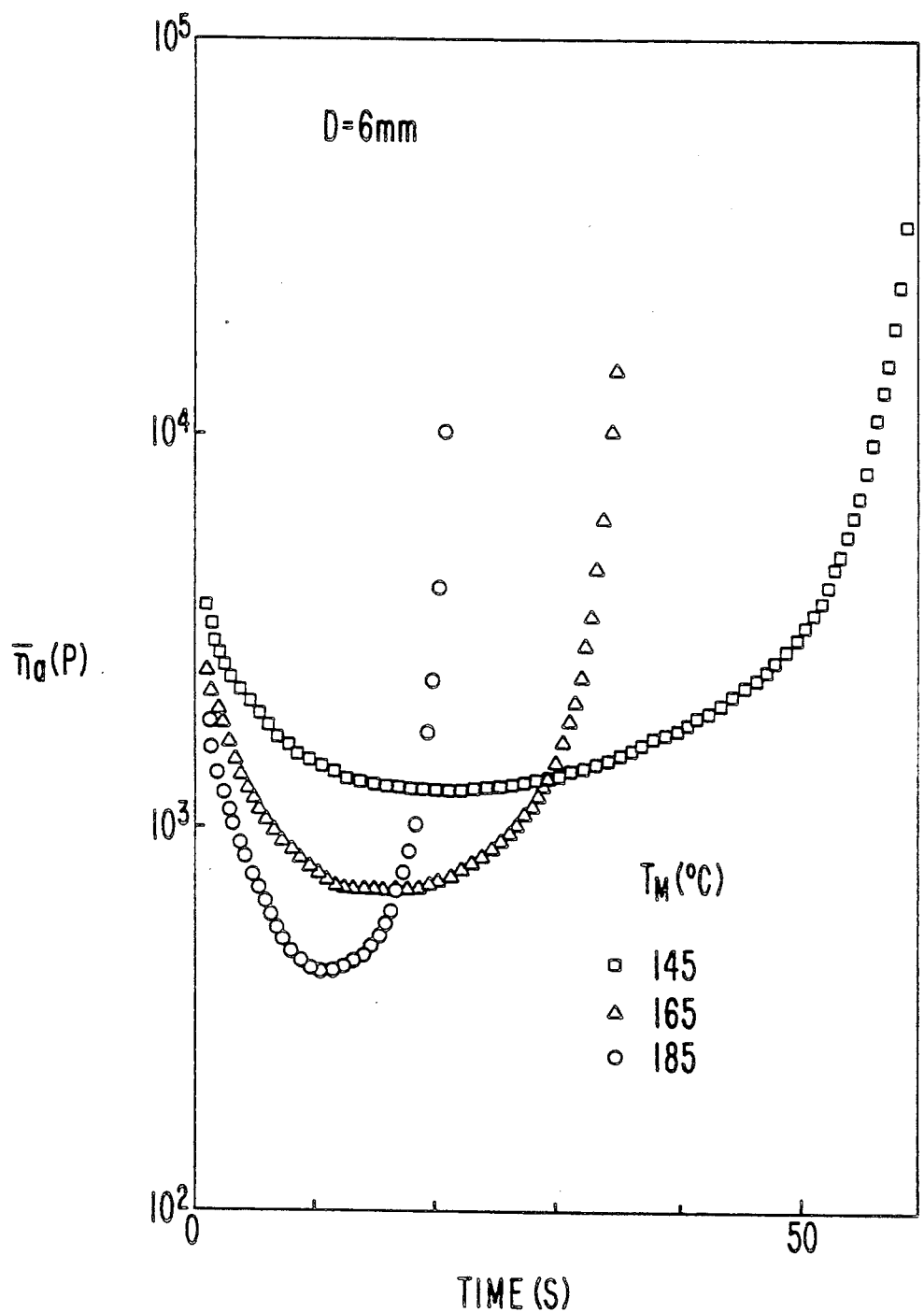

FIG. 10 graphically depicts a relationship between the average apparent viscosity $\eta a$ and the time of the individual temperatures $T_M$ where the circular flow passage 5 has a pipe diameter D equal to 6 mm (Table 1, flow passage No. 3). Comparing the relationship depicted in FIG. 10 with that of FIG. 9, it can readily be seen that when the pipe diameter D is 4 mm, the flow time is longer and the apparent average viscosity $\eta B$ is higher at the same individual temperature $T_M$.

Figure 11:
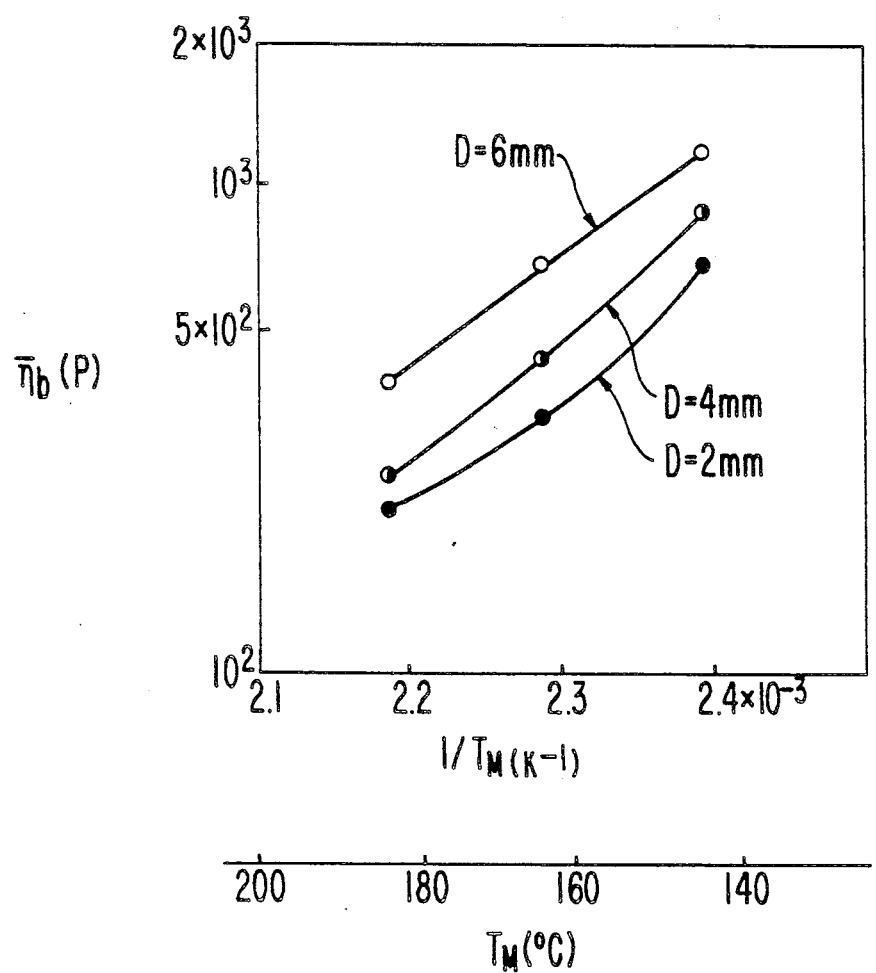
FIG. 11 is a graphical illustration of a relationship between a minimum value of an average apparent viscosity and a temperature of a metal mold.

FIG. 11 provides a graphical illustration of the relationship between the apparent average viscosity $\eta B$ and the individual temperatures $T_M$ for the individual pipe diameters D of 2 mm, 4 mm, and 6 mm. As shown in FIG. 11, a substantially linear relationship between log $\bar{\eta}b$ and $1/T_m$ is obtained for each pipe diameter D. It is possible to observe the apparent average viscosity $\eta b$ midway of a flow of resin through the circular pipe flow passage 5 since the difference between the temperature of the molding resin supplied to the pot 3 and the temperature of the metal mold M is large. Therefore, thermal transmission from the wall of the circular pipe flow passage 5 to the molding resin takes place in the flow passage 5, and at an initial stage of such flow, the apparent average viscosity $\bar{\eta}a$ is decreased due to melting.

If it is assumed that an ideal isothermal condition is obtained wherein the temperature of the molding resin becomes equal to a temperature of the metal mold M at an instant when the molding resin flows into the circular pipe flow passage 5 and, consequently, there is no influence of a thermal history until that time, then the value of apparent average viscosity $\bar{\eta}b$ is a characteristic value unique or peculiar to the molding resin which represents an initial viscosity of a viscosity curve at the individual temperature $T_M$.

Where the data of FIG. 11 involves a very small influence on a rise of viscosity by a curing reaction of the molding resin, if the apparent average viscosity $\eta_b$ where the pipe diameter D=0 mm., or, in other words, where the temperature of the metal mold M can be regarded as the temperature of the molding resin, is determined for each individual temperature $T_M$ by an extrapolation method, then it is considered that this is near to a relationship between an initial viscosity unique or peculiar to the molding resin and the individual temperature $T_M$. A relationship suggested in 1934 by E. N. doc Andrade between liquid viscosity M and absolute temperature T may be expressed as follows:

$$\eta = A \cdot \exp(B/T) = A \cdot \exp(E/RT),$$

where:
A & B = a constant,
E = apparent activation energy, and
R = gas constant.

Figure 12:
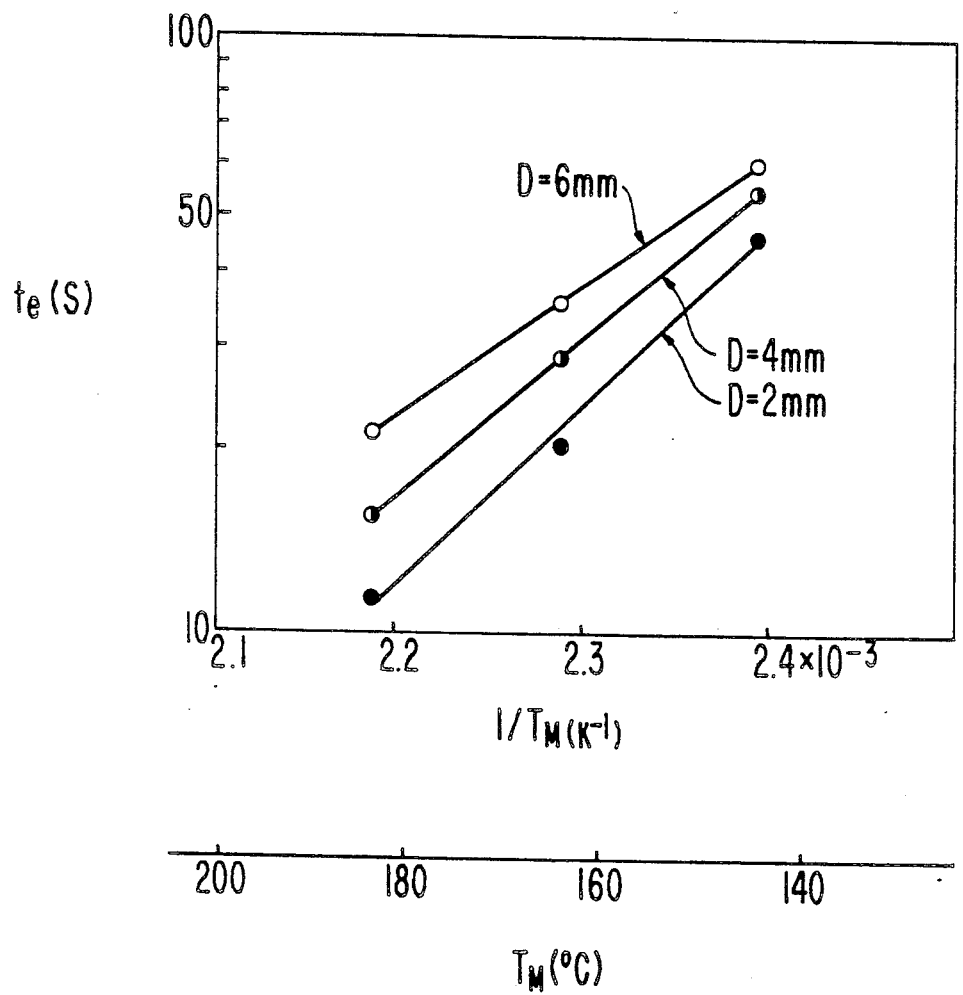
FIG. 12 is a graphical illustration of a relationship between an apparent gelation time and temperature of the metal mold.

Taking the above relationship into account, it can be seen that the constants A,B may be obtained graphically from a line expressing a direct proportion between the apparent average viscosity $\bar{\eta}_b$ and $1/T$ as apparent from FIGS. 11 or 12.

Applying the above relationship to resin flow an curing characteristics, it can be seen that the following relationship exists:

$$\eta_0 = a \cdot \exp\left(\frac{b}{T}\right) \quad (2)$$

where:
$\eta_0$ = an initial viscosity;
T = an absolute temperature; and
a and b = parameters peculiar or unique to the molding resin regarding an initial viscosity.

A relationship between the individual temperatures $T_M$ and an apparent gelation time $t_e$ for each pipe diameter D is illustrated in FIG. 12 and, as noted above, a substantially linear relationship is obtained between log $t_e$ and $1/T_M$ with any selected pipe diameter D. If it is assumed that experiments of an ideal isothermal condition could also be conducted here, then the apparent gelation time $t_e$ represents a value peculiar or unique to the molding resin of an isothermal viscosity curve at a given temperature. A relationship between a gelation time $t_e$ and the individual temperature $T_M$ can approximately be obtained by determining a value when the pipe diameter D=0 mm by an extrapolation method similar to the method for determining the apparent average viscosity $\bar{\eta}a$. Taking into account the above-noted relationship suggested by E. N. doc Andrade, the gelation time $t_e$ and individual temperature $T_M$, the relationship may be expressed in accordance with the following equation:

$$t_0 = d \exp\left(\frac{e}{T}\right) \quad (3)$$

where:
$t_0$ = a gelation time;
T = an absolute temperature; and
d and e = parameters peculiar or unique to the molding resin regarding the gelation time $t_0$.

Figure 13:
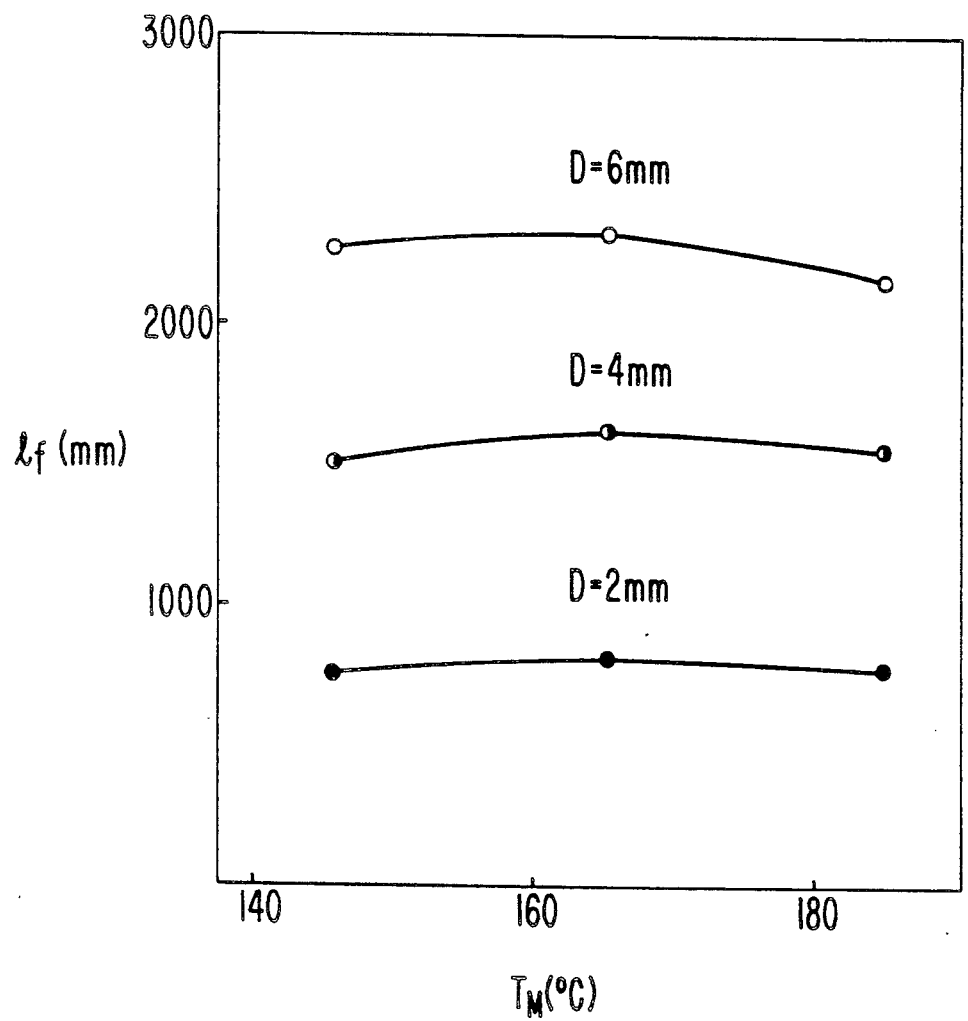
FIG. 13 is a graphical illustration of a relationship between a final flow distance and temperature of a metal mold.

A relationship between the individual temperatures $T_M$ and a final flow distance $l_f$ for each pipe diameter D is graphically depicted in FIG. 13. As shown in FIG. 13, as the pipe diameter D decreases, the final flow distance $l_f$ decreases. This occurs because, although the decrease in viscosity occurs faster as the pipe diameter D decreases, the resistance value of the circular pipe flow passage 5 increases in proportion to the pipe diameter D to a fourth power and the flow rate is decreased in accordance with such increase of the resistance to thereby further decrease the gelation time.

Meanwhile, where the pipe diameter D is identical, the final flow distance $l_f$ has a substantially proximate value at any individual temperature $T_M$ since the decrease in viscosity is rapid where the individual temperature $T_M$ is high, and while the flow distance $l_f$ increases during the time, the flow stopping time comes quickly and a reverse phenomenon takes place where the individual temperature $T_M$ is low to contribute to the same degree of the characteristic values of the final flow distance $l_f$.

In contradistinction to a widely-accepted, spiral flow test adopted by the Epoxy Molding Material Institute, a branch of the Society of Plastics Industry in the United States, for evaluation of a moldability of a thermosetting resin wherein only a value corresponding to the final flow distance $l_f$ is determined, in accordance with the present invention, it is possible to determine the final flow distance $l_f$ by utilizing information regarding the unique or peculiar flowing and curing conditions of the molding resin.

In order to rapidly and reasonably design or construct a flow passage of a metal mold and select molding conditions in an initial selection of a resin material to be used or in a particular production process, it is necessary to effect a flow simulation using characteristic values peculiar or unique to a molding resin obtained by the device of the present invention as input data, and such characteristic values can be determined in the following manner.

At first, an isothermal viscosity for a thermosetting molding resin may be determined in accordance with the following equation:

$$\eta(T) = \eta_0(T)\left(\frac{1 + t/t_0(T)}{1 - t/t_0(T)}\right)^{c(T)} \quad (4)$$

where:
 $\eta$ = a viscosity;
 $\eta_0$ = an initial viscosity;
 $t_0$ = a gelation time;
 c = a viscosity increase coefficient;
 T = an absolute temperature; and
 t = a time period.

Equation (4) may be simplified by taking the following equations into account:

$$\eta_0(T) = a\ exp(b/T)\ldots \quad (5)$$

$$t_0(T) = d\ exp(e/T)\ldots \quad (6)$$

$$c(T) = f/T - g\ldots \quad (7)$$

As readily apparent, equations (5) and (6) are the same as equations (2) and (3), respectively, and a, b, d, e, f and g are parameters peculiar or unique to a molding resin.

When the time period t in equation (4) is equal to 0, equation (4) satisfies the following boundary conditions: when t = 0, $$\eta = \eta_0(T)\ldots \quad (8)$$

when $t = t_0(T)$ $$\eta = \infty\ldots \quad (9)$$

Figure 14:
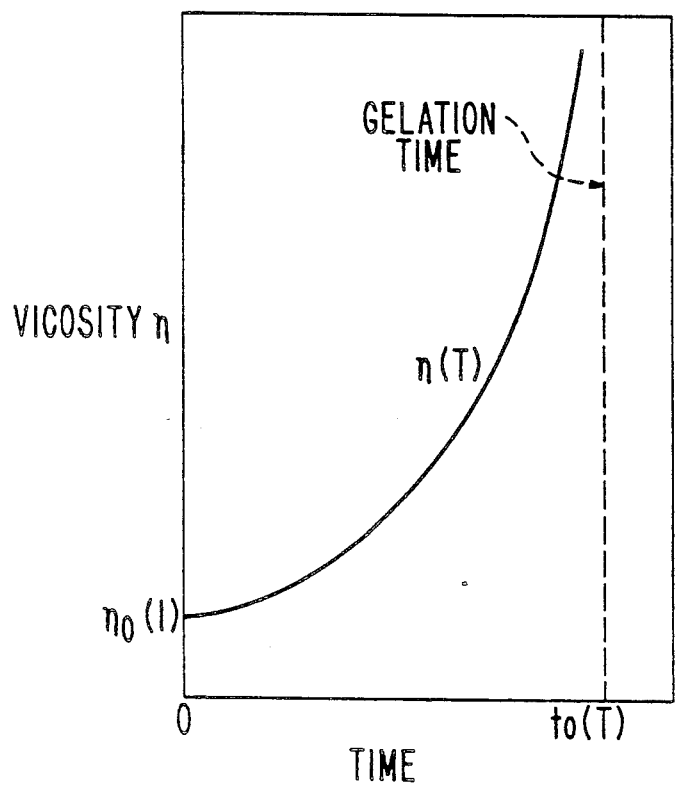
FIG. 14 is a characteristic view of an isothermal viscosity equation model.

The characteristics of equation (4) at an arbitrary temperature T are graphically depicted in FIG. 14.

Since the molding resin flows in a metal mold M while receiving heat from a wall of the pipe passage 5, in almost in all cases the molding resin is in a non-isothermal condition. A forecasting method of a viscosity in such an instance is described hereinbelow. At first, if the equation (4) is arranged dimensionlessly, then the following equation is obtained:

$$\mu = \frac{1 + \tau}{1 - \tau} \quad (10)$$

where:

$$\mu = \{\eta/\eta_0(T)\}^{1/c(T)}\ldots \quad (11)$$

$$\tau = t/t_0(T)\ldots \quad (12)$$

Figure 15:
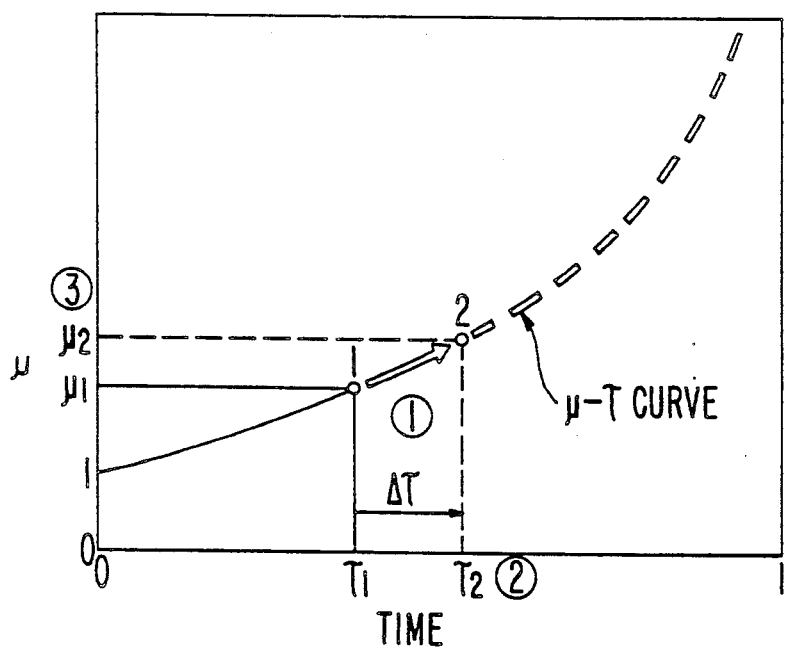
FIG. 15 is a graphical illustration of data for calculating a viscosity change in a non-isothermal condition.

A curve when $\mu = 1$ at $\tau = 0$ and $\mu = \infty$ at $\tau = 1$ has the characteristics shown in FIG. 15.

In FIG. 15 $\mu = \mu_1$ at $\tau = \tau_1$, and the time then is represented by $t_2$, then a new viscosity will be calculated when the time passes in time increments $\Delta t$ and the temperature also increases by temperature increments $\Delta T$ until the time and temperature reach $t_2$ and $T_2$ respectively. From equation (12) $\tau$ is a function of the time period t and the temperature T, and an increment $\Delta \tau$ or until a new condition $\tau_2$ may be calculated from the following equation:

$$\Delta \tau = \frac{\delta t}{\delta t}\Delta T + \frac{\delta t}{\delta T}\Delta T \quad (13)$$

The following equations can be obtained from equations (12) and (6):

$$\frac{\delta t}{\delta t} = \frac{1}{d\ exp(e/T)} \quad (14)$$

$$\frac{\delta t}{\delta T} = \frac{e}{T^2}\tau \quad (15)$$

Since $\Delta t$ and $\Delta T$ of equation (13) are known in advance as shown in FIG. 15, and $\Delta t$ can be determined, by substituting $T = T_1$ into equation (14) and $T = T_1$ and $\tau = \tau_1$ into equation (15), the following equation is obtained:

$$\tau_2 = \tau_1 + \Delta\tau\ldots \quad (16)$$

By substituting $\tau = \tau_2$ into the equation (10), $\mu_2$ may be determined in accordance with the following equation:

$$\mu_2 = \frac{1 + \tau_2}{1 - \tau_2} \quad (17)$$

From equation (11) the following equation can be obtained:

$$\eta_2 = \eta_0(T)\eta^{c(T)}\ldots \quad (18)$$

By substituting the values of $T = T_2$ and $\mu = \mu_2$ into equation (18), a new viscosity $\eta_2$ at a new condition can be determined by the following equation:

$$\eta_2 = \eta_0(T_1\ T_2)\mu_2{}^{c(T_2)}\ldots \quad (19)$$

By repeating the technique from $\tau = 0$ to $\tau = 1$, a change in viscosity $\mu$ from an initial stage in a nonisothermal condition for a gelation stage can be calculated.

In order to analyze a condition when the molding resin is flowing in a metal mold, it is necessary to solve the viscosity forecasting method described above and the fundamental equations of various principles of conservation below for a circular pipe passage:

$$Q = 2\pi \int_0^R v_z \gamma dZ \quad (20)$$

$$\frac{\partial P}{\partial Z} = \frac{1}{\gamma}\frac{\partial}{\partial \gamma}\left(\gamma\eta\frac{\partial v_z}{\partial \gamma}\right) \quad (21)$$

$$PC\left(\frac{\partial T}{\partial t} + V_z\frac{\partial T}{\partial Z}\right) = \frac{1}{\gamma}\frac{\partial}{\partial \gamma}\left(\gamma\lambda\frac{\partial T}{\partial \gamma}\right) + \quad (22)$$

$$\eta\left(\frac{\partial v_z}{\partial \gamma}\right)^2$$

where:
 Q = a flow rate;
 R is a radius of a circular pipe;
 $v_z$ is a flow rate in a direction of a pipe axis;

$\gamma$ = distance in a diametrical direction of the pipe;
Z = a distance in a direction of the pipe axis;
P = a pressure;
$\eta$ is a viscosity;
C = density concentration;
T = a temperature;
t = a time period; and
$\xi$ = a coefficient of thermal conductivity.

It is noted that equations (20), (21) and (22) respectively represent equations of continuity, principles of conservation of momentum and energy.

Figure 16:
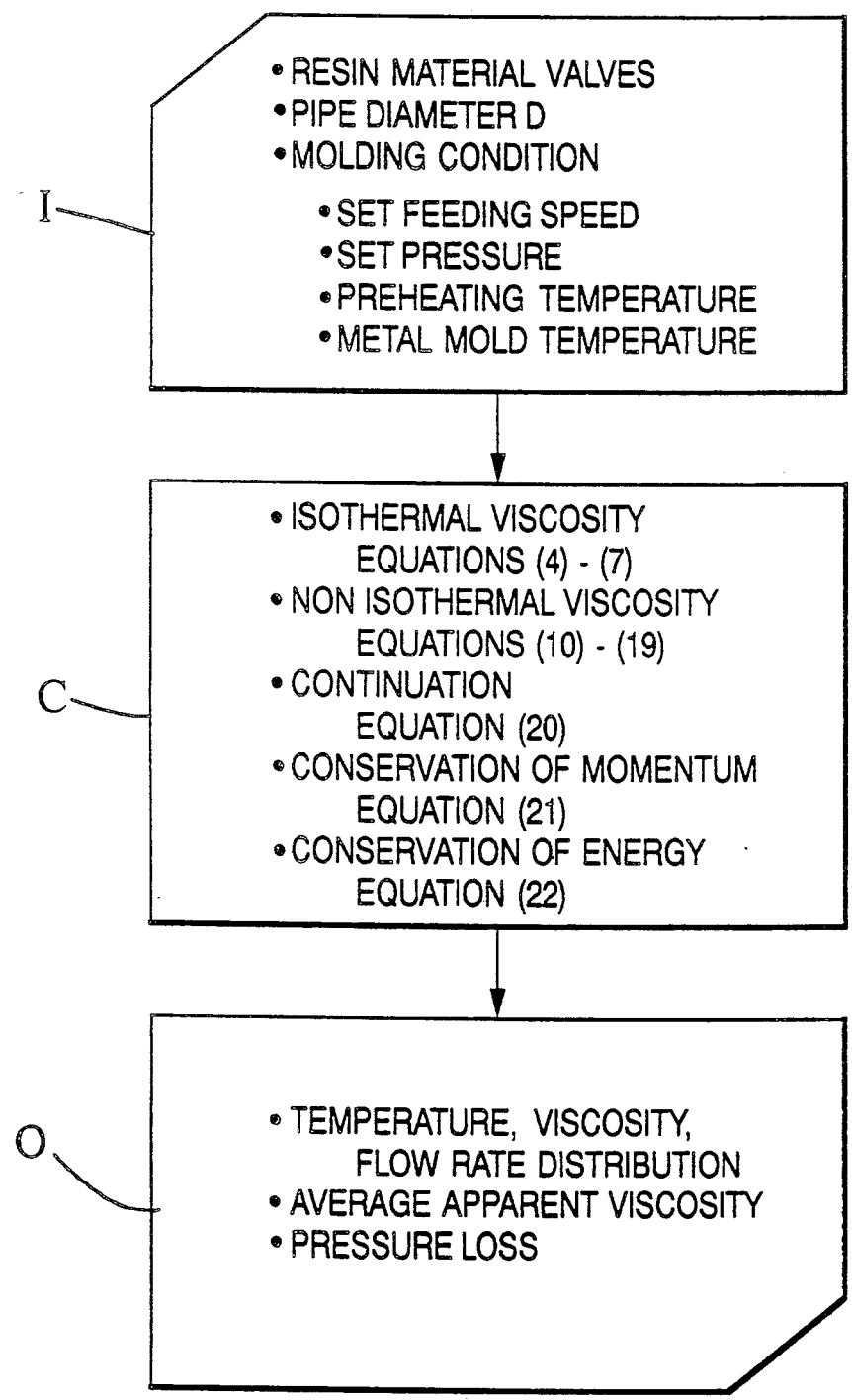
FIG. 16 is a general flow chart of a molding resin flow simulation.

If equations (20) to (22) are solved by a numeral analysis method such as differential calculus of a finite element method under given initial and boundary conditions in combination with the isothermal viscosity equations (4) to (7) and the nonisothermal viscosity forecasting method equations (10) to (19), then a flow simulation in a circular pipe flow passage can be conducted with an outline of a simulation program using an input I, calculation C, an output 0 in accordance with the present invention being illustrated in FIG. 16. An average apparent viscosity may also be obtained as an output 0 and, consequently, comparison can then be made between calculated values of a result of the simulation program and actually measured values graphically illustrated in FIGS. 8-10.

In the simulation technique of the present invention, the viscosity equations may, for example, take into account six parameters, namely, parameter a, b, d, e, f, and g in the relationships expressed in equations (5) to (7), and it is important to determine the values of these parameters sufficiently. Estimating values of the parameters a-g from data illustrated in FIGS. 8-12 obtained by the device of the present invention is described more fully hereinbelow.

Figure 17A:
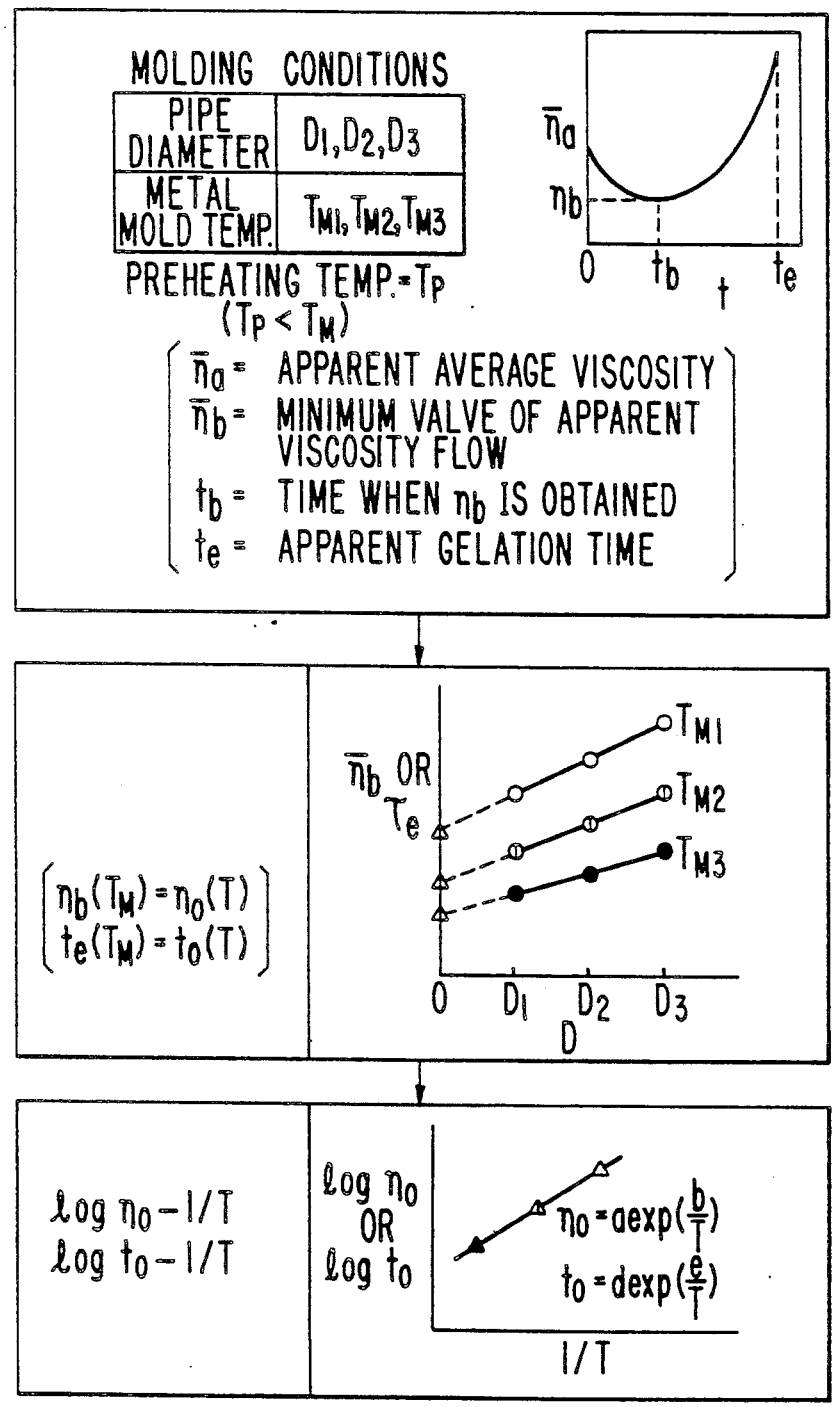
FIGS. 17A and 17B are flow charts explaining an estimation of flow and curing parameters of a molding resin.

More particularly, a method of estimating values of the parameters a, b, d, and e is diagrammatically depicted in FIG. 17A. The method for estimating the values of the parameters a, b, d, and e is described hereinabove in connection with FIGS. 11 and 12.

In FIG. 17A, the values of the minimum apparent average viscosity $\bar{\eta}_b$ and apparent gelation time $t_e$ are read or obtained from data of the change of the average apparent viscosity $\nu_a$ when the diameter D of the flow passage pipe 5 and the individual temperature $T_M$ of the metal mold M are changed, and the values of the apparent average viscosity $\bar{\eta}_a$ and apparent gelation time $t_e$ for each individual temperature $T_M$ are obtained by an extrapolation method corresponding to a situation wherein the pipe diameter D = 0 mm, with the following relationships being valid:

$$\bar{\eta}_b(T_M) = \eta_0(T)$$

$$t_e(T_M) = t_0(T).$$

The values of the parameters a, b, d and e may be estimated from the following relationships which are graphically depicted in FIG. 17A:

$$\log \bar{\eta}_0 - 1/T$$

$$\log t_0 - 1/T.$$

Figure 17B:
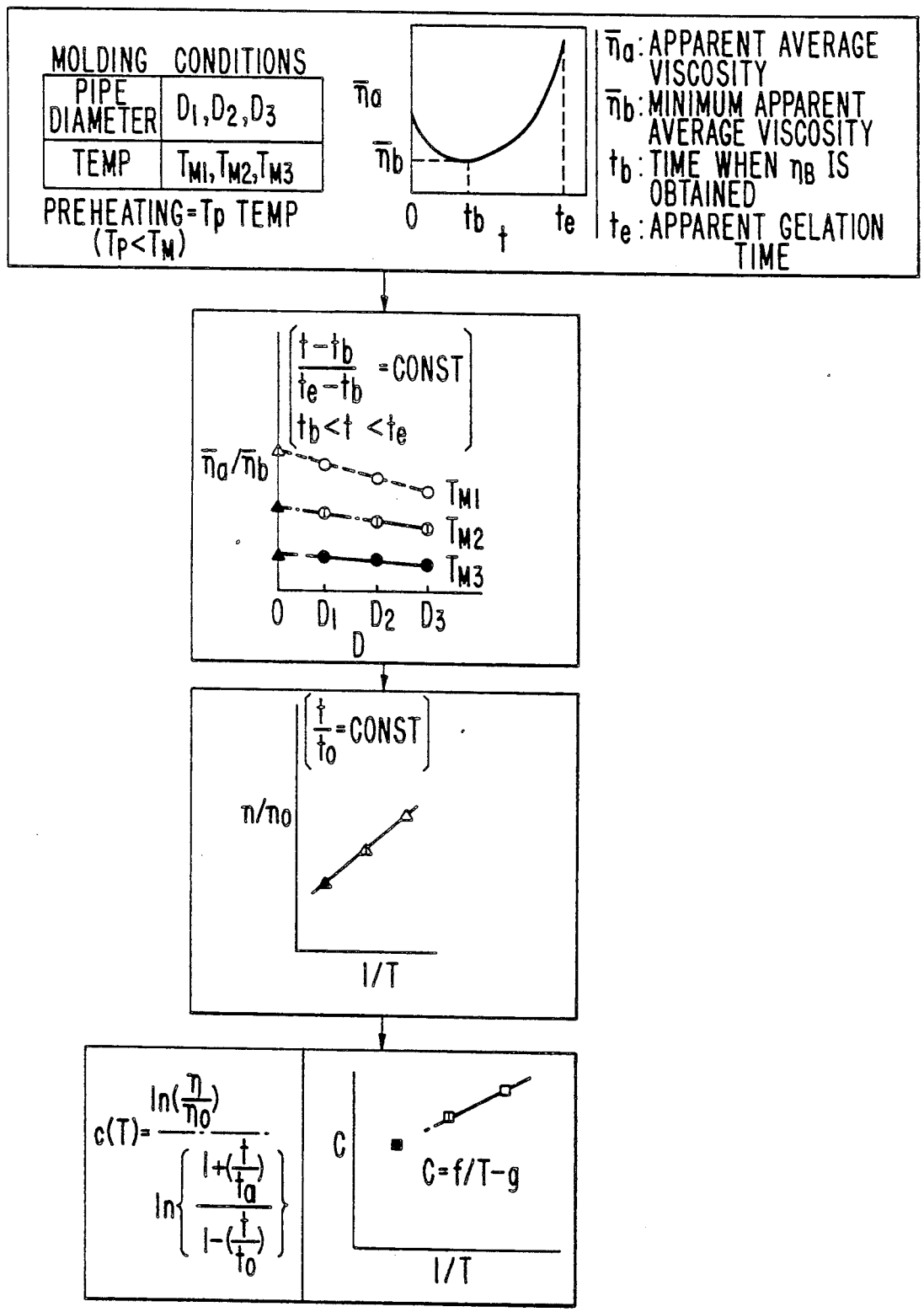

FIG. 17B provides a graphic illustration of steps for determining the parameters f and g, with the method involving a performing of a conversion of data into dimensionless data as well as an operation of deformation of equation (4) simultaneously utilizing a viscosity increase curve produced between the time $t_b$ and apparent gelation time $t_e$ and estimating characteristic values by an extrapolation method corresponding to a situation wherein the pipe diameter D = 0 mm.

More particularly, the dimensionless viscosities $\bar{\eta}_a/\bar{\eta}_b$ are calculated at a dimensionless time when $(t-t_b)/(t_e-t_b)$ present fixed values $(t_b<t<t_e)$ in individual conditions. Values of $\bar{\eta}_a/\bar{\eta}_b$ corresponding to those values where the pipe diameter D = 0 are calculated for each individual time $T_M$ and, in this instance, $\bar{\eta}_a(T_M)/\bar{\eta}_b(T_M)$ can be regarded as $\bar{\eta}(T)/\bar{\eta}_0(T)$.

A relationship between the temperature T and $\eta/\eta_0$ may be graphically determined as illustrated in FIG. 17B where the value of $t/t_0$ is constant. By substituting the values of $\eta/\eta_0$ and $t/t_0$ for each T it is possible to determine the value of C, with the values of the parameters f and g being estimated from the relationship between C and $1/t$ illustrated in FIG. 17B.

It is to be noted that the reason for employing the above-described complicated technique is that the material for encapsulating electronic components exhibits a very rapid curing time and an experimental determination of an ideal isothermal condition is very difficult. Subsequently, a flow simulation may be conducted using the values of the parameters a, b, d, e, f, and g estimated by the techniques outlined in FIGS. 17A and 17B and thus calculated values and actually measured values of the apparent average viscosity $\eta_a$ are compared with each other. Then the values of the parameters a, b, d, e, f and g are finally corrected by a curve fitting method such as the method of least squares so that the calculated values may approach the actual measured values, and the values of the parameters are determined when an error which can be considered reasonable is reached. The values of the parameters of the resin determined by the above-described techniques are shown in Table 2 below.

TABLE 2

| Item | Symbol | | Value |
|---|---|---|---|
| density | $\rho$ | $\frac{g}{cm^3}$ | 1.82 |
| Specific Heat | c | $\frac{cal}{g \cdot k}$ | 0.25 |
| Heat Conductivity | $\lambda$ | $\frac{cal}{cm \cdot sec \cdot k}$ | $1.96 \times 10^{-3}$ |
| Parameters in Viscosity Equations | a | (poise) | $3.28 \times 10^{-8}$ |
| | b | (k) | 9,783 |
| | d | (sec) | $1.474 \times 10^{-7}$ |
| | e | (k) | 8,185 |
| | f | (k) | 2,004 |
| | g | (—) | 3.5 |

Figure 18:
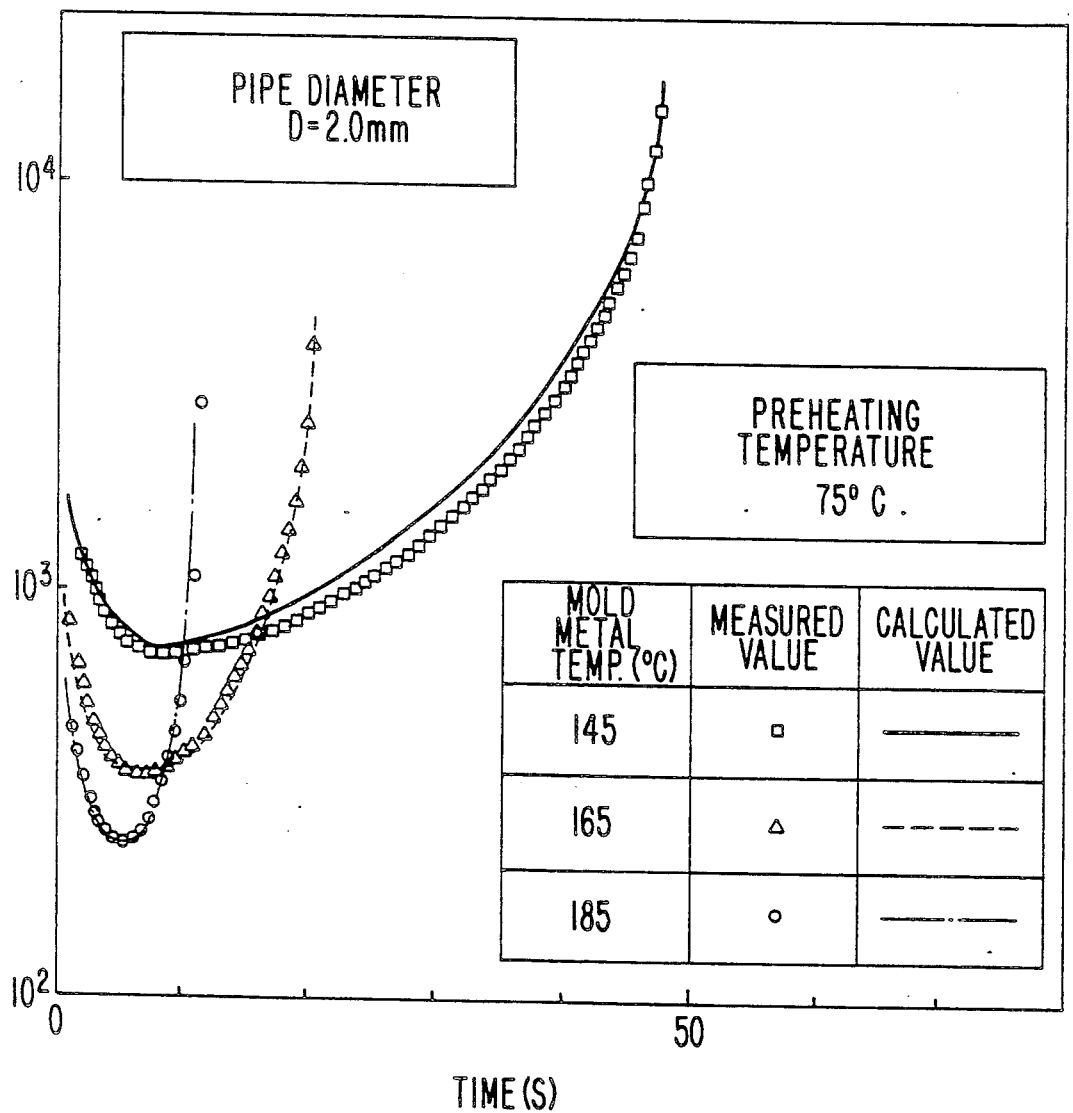
FIG. 18 is a graphical comparative illustration between measured values and calculated values of an average apparent viscosity.

The values in Table 2 represent input data for a flow simulation in dependence upon the resin used. A comparison between measured values and calculated values by a simulation of the apparent average viscosity $\eta_a$ is graphically illustrated in FIG. 18. As apparent from FIG. 18, the measured value and calculated values by a simulation of the apparent average viscosity $\eta_a$ exhibit a very high conformity with respect to each other at each individual mold temperature, and the graphical illustration of FIG. 18 verifies the feasibility of the subject matter of the present invention.

In accordance with the present invention, flow and curing parameters to a thermosetting resin which are not influenced by measurement conditions can reasonably be determined with a high degree of accuracy.

Moreover, by analyzing the above-defined viscosity equations and the above-described forecasting methods of a change in apparent average viscosity in accordance with the present invention in combination with the above-noted equations of the various principles of conservation in accordance with the configuration of the metal mold for mass production using the values of the parameters thus determined as input data, a flow simulation is possible for any condition, and optimum dimensions of a flow passage of a metal mold for mass production and optimum molding conditions can be determined on the desk-type basis, that is, without an experimental production. Moreover, a checking of a moldability in the development of a resin and lot management of a molding resin can also be greatly facilitated.

Figure 19:
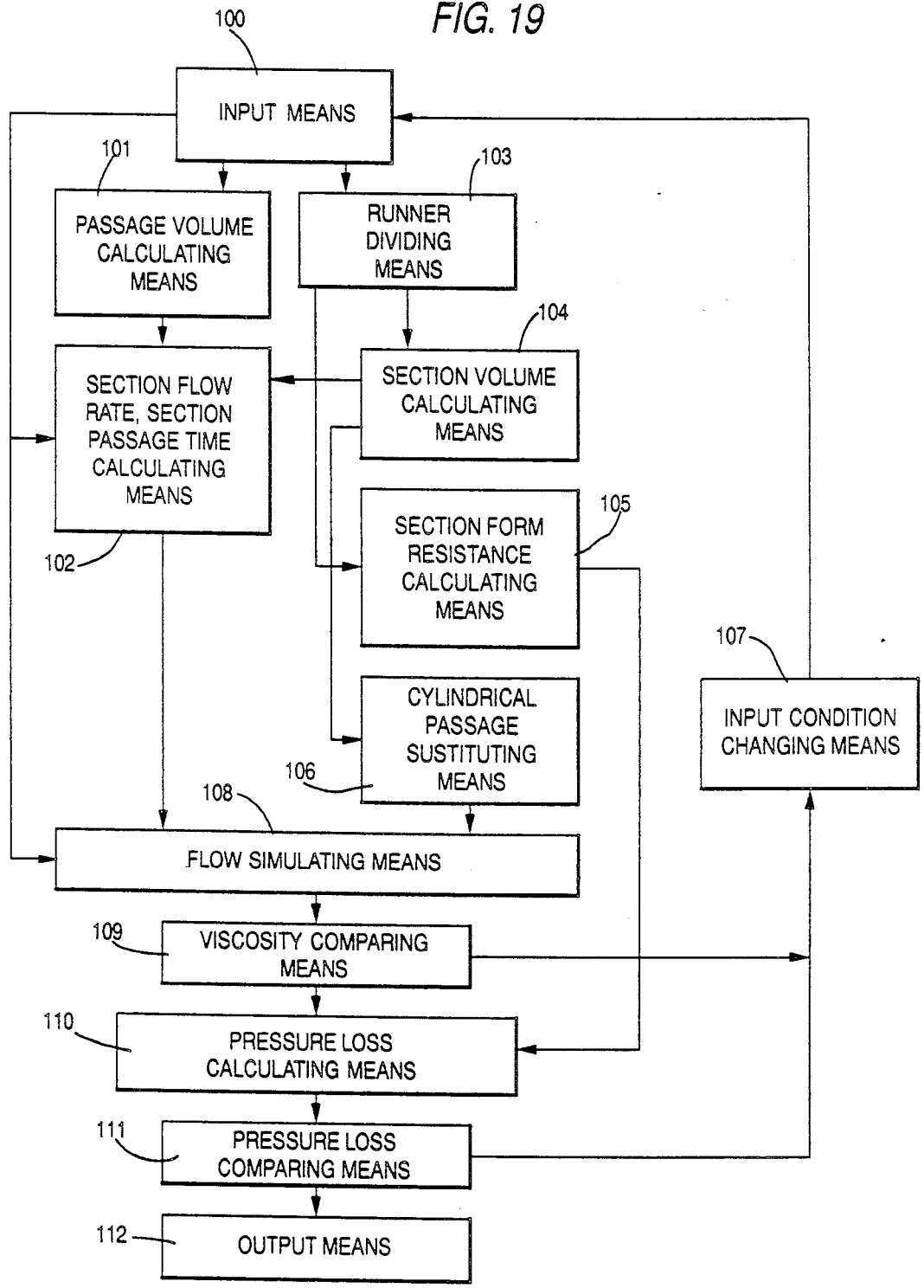
FIG. 19 is a schematic illustration of an analysis system constructed in accordance with the present invention.

FIG. 19 provides a schematic representation of an analyzing system for the estimation of a mode of flow of a resin within a metal mold, data necessary for simulation including physical properties of the resin, molding conditions and dimensions of the runner of the mold are supplied to an input means 100. The input means 100 provides a data output of the runner to a runner dividing means 103 and runner volume calculating means. Then the runner volume calculating means calculates an entire volume of the runner, with the runner dividing means dividing the runner into sections. The section volume calculating means 104 processes the output data of the runner dividing means 103 to determine a volume of each section, and a form resistance calculating means processes the same output data to determine a form resistance of each section. A cylindrical passage substituting means 106 processes the output data of the section volume calculating means to convert each section into a combination of cylindrical runners.

Output data of the passage volume calculating means 101, output data of the section volume calculating means 104, and transfer time data from data of molding conditions supplied to the input means 100 are supplied to a section flow rate and section passage time calculating means 102. The section flow rate and section passage time calculating means 102 calculates the flow rate of the molding resin in each section and a second passage time at which the molding resin passes through predetermined sections A flow simulating means 108 simulates the mode of flow of the molding resin through the cylindrical runners on the basis of the output data of the section flow rate and section passage time means 102, output of the cylindrical passage substituting means 106, and data of molding conditions supplied to the input means 100 to determine the temperature, viscosity, flow speed and mean or average apparent viscosity of the molding resin in each section of the runner.

The results of the operation of the flow simulating means 108 is supplied to a viscosity comparing means 109. When the results of a comparison by the viscosity comparing means 109 are unsatisfactory, the simulation is interrupted and then an input condition changing means 107 alters or changes a portion of the input data supplied to the input means 100 and another cycle of simulation is initiated. When the result of the comparison by the viscosity comparing means 109 is satisfactory, a pressure loss calculating means 110 processes the data obtained through the simulation, namely, the mean apparent viscosity, the flow rate and form resistance for each section, to determine pressure loss in each section and overall pressure loss, namely, a sum of the pressure losses in all sections.

The pressure loss calculating means 110 provides an output of the calculation to a pressure loss comparing means 111. When the calculated pressure loss in each section and the calculated overall pressure loss are greater than predetermined values, the pressure loss comparing means 111 provides an output signal to the input condition changing means 107 to initiate another cycle of simulation. When the result of the pressure loss comparison is satisfactory, an output unit 112 provides a final data output including the dimensions of the runner, molding conditions, and other necessary pertinent data.

Figure 20A:
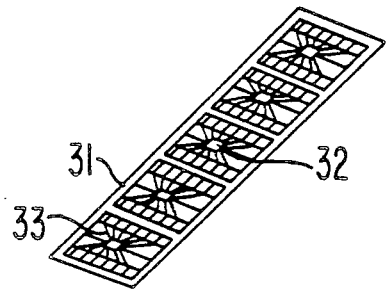
FIG. 20A is a plan view of a multiple lead frame of a semiconductor device.

FIGS. 20A–20D somewhat schematically illustrate different stages of a manufacturing process for a resin-sealed semiconductor device. More particularly, as shown in FIG. 20A, a plurality of semiconductor chips 32 are mounted on and connected on by gold leads 33 to a multiple lead frame 31 to form a plurality of semiconductor devices, with one of the semiconductor devices being more clearly illustrated in FIG. 20B.

Figure 20B:
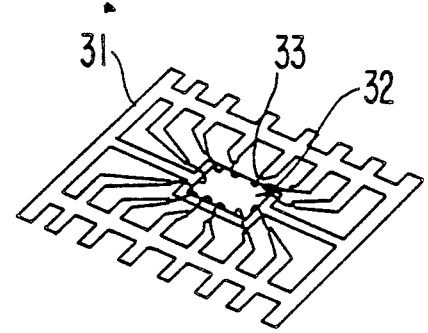
FIG. 20B is an enlarged detailed view of a portion of the semiconductor device of FIG. 20A.
Figure 20C:
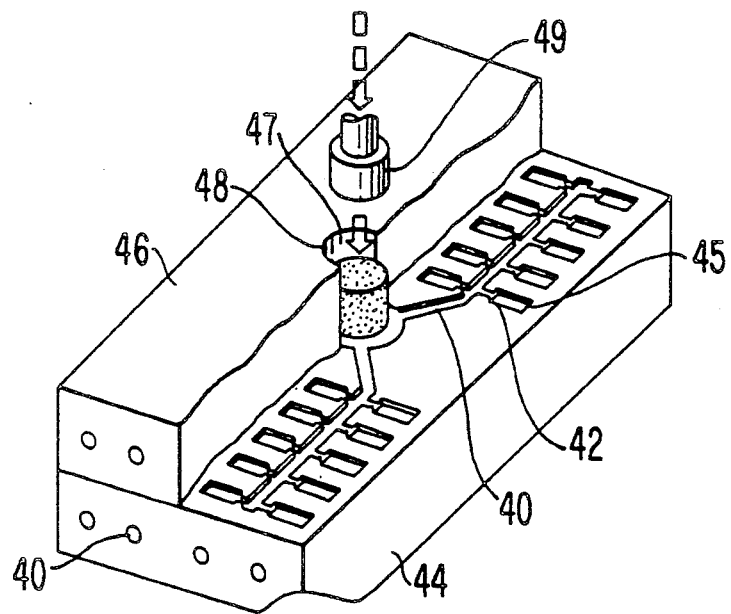
FIG. 20C is a schematic representation of a process of sealing the semiconductor devices of FIG. 20A in a resin.

As shown in FIG. 20C, the multiple lead frames 31, each mounted with semiconductor chips 32, are placed in mold cavities 45 formed in a bottom half mold 44. Then an upper half mold 46 is brought into engagement with the bottom half mold 44 to secure the multiple lead frames 31 in the mold cavities 45. A pot 48 is charged with pellets of a thermosetting resin 47 preheated by a high frequency preheater (not shown). The thermosetting resin 47 is melted by heat transfer thereto from the metal mold heated by a heater 40, and then a plunger 49 of a molding machine (not shown) is forced downwardly to inject to molten resin 47 through runners 41 and gates 42 into the mold cavities 45.

Figure 20D:
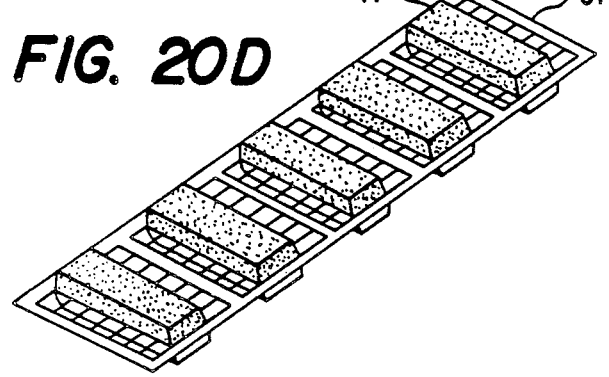
FIG. 20D is a perspective view of resin sealed semiconductor devices obtained from the process of FIG. 20C.

In a predetermined time period after the mold cavities 45 have been filled with molten resin 47, the molten resin 47 solidifies. Then, the upper half mold 46 is separated from the lower half mold 44 to eject resin-sealed devices such as shown in FIG. 20D.

Figure 20E:
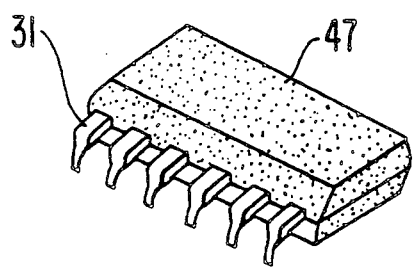
FIG. 20E is a perspective view of an individual resin sealed semiconductor device obtained in accordance with the present invention.

Thereafter, the multiple lead frame 31 is cut to separate the semiconductor devices, and portions of the lead frame 31 of each device are bent so as to result in a finished semiconductor device such as illustrated in FIG. 20E. A difference between the cavities 45 in resin filling rate causes a difference between the cavities 45 in the viscosity, flow velocity and solidifying mode of the thermosetting resin 47 and the resultant formation avoids in the molding and deformation of the gold leads 43. Consequently, the thermosetting resin 47 must be introduced into the cavities 45 at equal charging rates. By virtue of the abovedescribed principles and techniques in accordance with the present invention, it is possible to design and construct runners capable of introducing the molten thermosetting resin 47 at equal charging rates into a plurality of mold cavities 45.

More particularly, in accordance with the present invention, a thermosetting resin 47 may be distributed uniformly to a plurality of mold cavities 45 by determining the dimensions of the runners 41 on the basis of an estimated pressure loss in the runners 41 so that the sums of each pressure loss in the runner 41 and pressure loss in a gate 42 corresponding to each mold cavity 45 are the same. In this connection, the runners 41 and gates 42 of FIG. 20B each have a cross-section with the shape of a semi-circle or inverted trapezoid and, in most cases, the sectional area of each runner 41 varies with the length of the same. A simulation of the flow of thermosetting resin 7 employing the foregoing complicated boundary conditions requires an enormous calculating time and, consequently, such a manner of simulation is not applicable to a practical design operation. Accordingly, in order to simplify the calculation for simulation, the present invention utilizes the simulation procedure discussed more fully hereinbelow.

In accordance with the present invention, the runner 41 is divided into a plurality of sections, with a specific form resistance $\beta$ of each section and flow rate Q in the same being calculated. Each section is substituted by a cylindrical passage, and a flow of resin through the cylindrical passage is simulated to calculate the temperature, viscosity, flow velocity and mean apparent viscosity $\eta_a$, with the pressure loss $\Delta P$ being calculated by the following equation:

$$\Delta P = \beta \cdot \eta_a \cdot Q \ldots \quad (20)$$

Figure 21A:
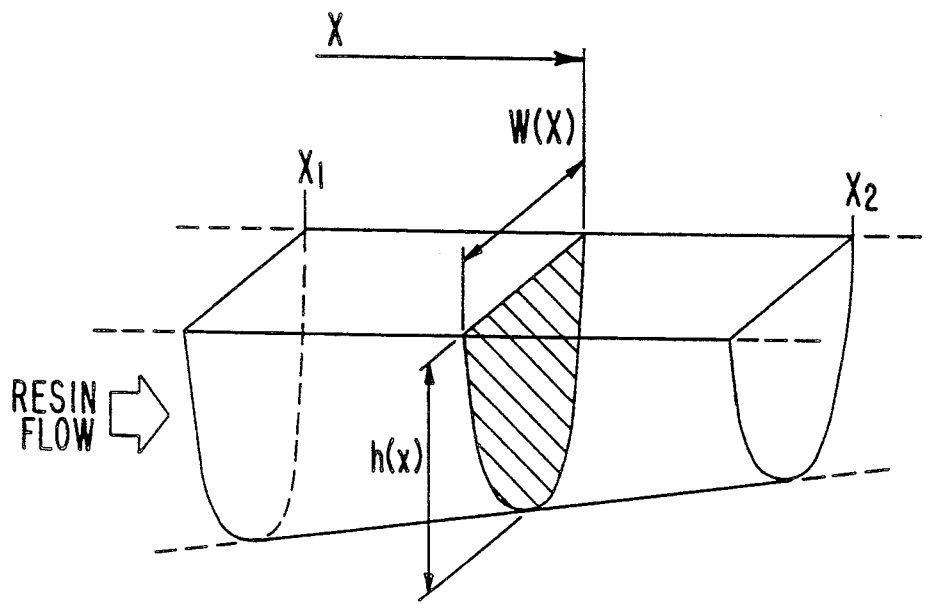
FIGS. 21A and 21B are schematic illustrations for depicting a method of calculating pressure loss in a runner of a metal mold.

FIG. 21A provides an illustrative example of a section varying in sectional area from one end thereof to the other. In FIG. 21A, X represents a distance of a section from a reference point, with $X_1$ and $X_2$ respectively representing a starting end and terminal end of the section, and W representing the width of the passage, with h being a depth of the passage. The width W and the depth h are functions, respectively of the distance X. When W<h, the following relationship is valid:

$$\beta_{X_1 \sim X_2} = \int_{X^1}^{X^2} 12/(W(X)h^3(X)F(X))dX \quad (21)$$

where:
F = a shape factor dependent upon a ratio between the width W and depth H.

The value of $\beta$ can be determined through analytical approximation of approximate integration using Simpson's rule or the like by representing the width W, the depth h and the factor F, respectively, by functions of X and, when W<h, the following relationship is valid:

$$\beta_{X_1 \sim X_2} = \int_{X^1}^{X^2} 12/(W^3(X)h(X)F(X))dX \quad (22)$$

When the section has both a portion where W≧h, and a portion where W<H, the relationships (21) and (22) are accordingly applied and the results of the calculation are totalled.

Figure 21B:
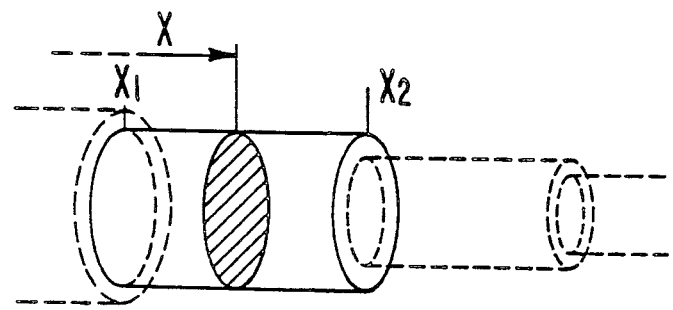

FIG. 21B provides a representation of a cylindrical passage equivalent to the section shown in FIG. 21A. In FIG. 21B, the section between $X_1$ and $X_2$ represents a cylindrical passage having a uniform diameter, with the diameter of the cylindrical passage being determined so that the section illustrated in FIG. 21A and cylindrical passage of FIG. 21B have the same volume. In FIG. 21B, cylindrical passages equivalent to the sections before and after the section shown in FIG. 21A of the runner tapering in a direction of flow of the resin are indicated by phantom lines.

The above-described procedure of flow simulation of the cylindrical passage is also applicable to estimating the mean apparent viscosity $\bar{\eta}_a$ in each section. In this connection, the flow rate Q in each section is calculated by calculating or determining $Q_p$ and dividing $Q_p$ by the number of branches, with $Q_p$ being determined in accordance with the following relationship:

$$Q_p = V_f/t_p.$$

where:
$Q_p$ = injection rate from the pot 48,
$V_f$ = volume of the runners 41, and
$t_p$ = resin injecting time of the plunger 49.

Thus, a pressure loss in each section of the runner 41 is determined and the overall pressure loss $\Delta P_T$ is determined by summing up or totalling the pressure losses in all sections.

Figure 22:
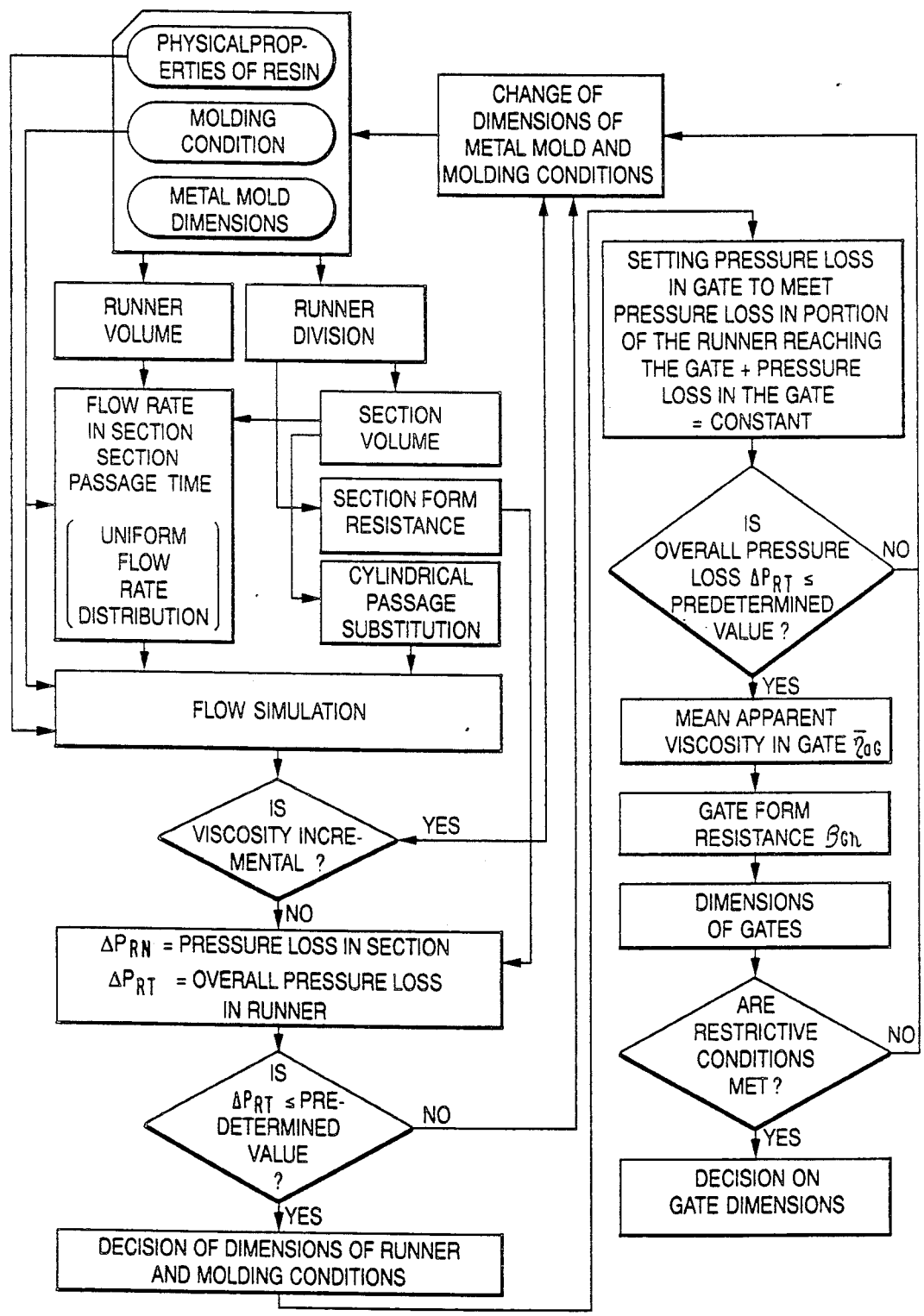
FIG. 22 is a flow chart depicting a procedure for designing and constructing runners and gates of a metal mold provided with a plurality of mold cavities.

FIG. 22 provides an example of a flow chart of procedure for designing runners 41 and gates 42 for a metal mold having a plurality of mold cavities 45 as shown in FIG. 20A so that the thermosetting resin is introduced into the mold cavities 45 at equal charging rates. As shown in FIG. 22, first input data including physical properties of the thermosetting resin 7 such as shown in Table 2, molding conditions and dimensions of the metal mold are given. The molding conditions include the resin injecting time $t_p$ of the plunger 49, maximum injection pressure $P_M$ of the molding machine, a resin preheating temperature, and the temperature of the metal mold. The dimensions of the metal mold includes fixed values such as pitch of the mold cavities 45 and the layout of the runners 41, as well as temporary values for the rest of the dimensions. Then the overall volume $V_f$ of the runners 41 is calculated and each runner is divided into sections so that the number of junction planes between adjacent sections is at least equal to the number of branches branching from the runner 41 and the flow of thermosetting resin 7 is not branched in the sections. Then the volume $V_N$ and form resistance $\beta_N$ of each section are calculated.

Resin injection rate, namely, resin discharge rate of the pot 48 is calculated by using the above-noted relationship $Q_p = V_f/t_p$, and then $Q_p$ is divided by the number of branches to determine the flow rate $Q_n$ of the thermosetting resin 47 in each section on a premise that the thermosetting resin 47 is distributed to the mold cavities 45 at equal flow rates. Then, a passage time $t_n = V_n/Q_n$ for each section, namely, a time in which the thermosetting resin 47 flows through each section, is calculated, with the diameter of a cylindrical passage having the volume $V_n$ being then determined for each section. Then the flow modes of the thermosetting resin 47 and the cylindrical passages are simulated sequentially in order of the cylindrical passages with respect to the direction of flow of the thermosetting resin 7 to calculate the temperature, viscosity $\eta$, flow velocity distribution and mean or average apparent viscosity $\bar{\eta}_a$ of the thermosetting resin 47 in each section.

The viscosity $\eta$ of the thermosetting resin 47 before a predetermined radial position and the viscosity $\eta$ of the thermosetting resin 47 after the radial position in each section are compared to determine if the latter viscosity $\eta$ is higher than the former viscosity. If the viscosity $\eta$ after the predetermined radial position is higher than the viscosity before the predetermined radial position, the molding conditions and dimensions of the metal mold are changed, and then the same calculations are repeated.

The above adverse variation of the viscosity $\eta$ of the thermosetting resin 47 is due to the excessively advanced hardening reaction of the thermosetting resin 47 prior to flowing into the mold cavities 45, and the supply of such inexcessively hardened thermosetting resin 47 having a high viscosity into the molding cavities 45 is highly likely to produce faulty moldings. After the requirement concerning the viscosity $\eta$ of the thermosetting resin 47 has been satisfied, a pressure loss $\Delta P_{Rn}$ in each section of the runner 41 is calculated in accordance with the following relationship:

$$\Delta P_{Rn} = \beta_n \cdot \eta_{an} \cdot Q_n.$$

Then the pressure losses are totalled or summed to obtain a pressure loss $\Delta P_{RT}$ in the runner 41. The calculated pressure loss $\Delta P_{RT}$ is compared with a reference pressure loss $\Delta P_{RT}$ is compared with a reference pressure loss $\Delta P_{RS}$ and, when $\Delta P_{RS} \leq \Delta P_{RT}$, at least one of the data representing the dimensions of the runner 41 of the metal mold, the resin injecting time of the plunger 49, the resin preheating temperature and temperature of the metal mold is changed and the pressure loss $\Delta P_{RT}$ is once again calculated on the basis of the new data.

The above procedure is repeated until the dimensions of the runner and molding conditions meeting the inequality of $\Delta P_{RS} > \Delta P_{RT}$ are determined. Unless $\Delta P_{RS} > \Delta P_{RT}$ is satisfied, namely, when the pressure loss approaches a maximum injection pressure $P_M$, the plunger 49 is unable to move into the pot 48 at a constant speed and thereby the thermosetting resin 47 flowing through the runner 41 is liable to stagnate thereby causing a faulty molding operation. As a practical matter, $\Delta P_{RS}$ is far smaller than $P_M$. Then, a temporary pressure loss in each gate 42 is selected so that the sum of pressure losses in a portion of the runner 41 reaching the corresponding cavity 42 and pressure loss in the same gate 42 coincide with a constant. When a calculated overall pressure $\Delta P_T$ is equal to or greater than a predetermined pressure loss $\Delta_S$, some of the molding conditions and the dimensions of the mold are changed and the pressure loss is once again calculated, with the calculation being repeated until $\Delta_S > \Delta P_T$ is met, and then a pressure loss $\Delta P_{Gn}$ is determined.

When the value of $\Delta P_S$ is in the range of $\Delta P_S$ to $P_M$, then a form resistance $\beta_{Gn}$ to be given for each gate is calculated by substituting the value $\Delta P_{Gn}$, the value of average apparent viscosity $\bar{\eta}_{aG}$ for each gate 42 obtained through the simulation of the flow of the thermosetting resin 47 and the value of the flow rate $Q_{Gn}$ through each gate 42 into the following expression:

$$\beta_{Gn} = \Delta P_{Gn}/\bar{\eta}_{aG} \cdot Q_{Gn}.$$

Then the dimensions of the gates 42 are calculated by utilizing the equations (21) and (22). If the calculated dimensions of the gates 42 do not meet restrictive conditions for the respective gates 42, such as, for example, the upper and lower limits of an angle for a portion tapering in a direction of flow of the thermosetting resin 47 and the upper and lower limits of depth for the same portion, some of the dimensions of the metal mold and molding conditions are changed to obtain dimensions for the gates 42 meeting the restrictive conditions.

FIGS. 23A–23D respectively illustrate the relationship between the runner 41 and gates 42 of FIG. 20B constructed in accordance with the present invention. For the sake of clarity, the pot 48, portion of the runner 41 radially extending from the pot 48, and the cavities 45 shown in FIG. 20B are admitted for the sake of clarity. As shown most clearly in FIG. 23B, a depth of the runner 11 is decreased gradually toward the extremity thereof so that the molten thermosetting resin reaches the cavities $C_1$, $C_2$, $C_3$, $C_4$, $C_5$ with the least time difference between the cavities.

Figure 23A:
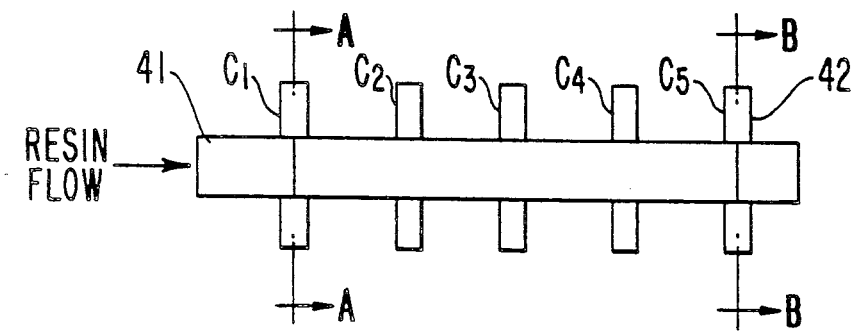
FIGS. 23A, 23B, 23C and 23D are schematic views of runners and gates of a metal mold.
Figure 23B:
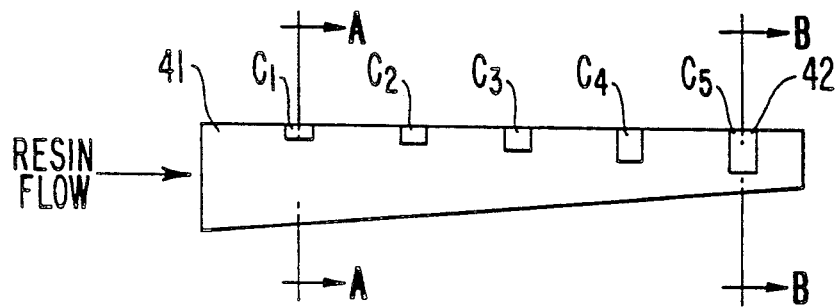
Figure 23C:
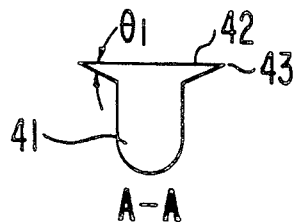
Figure 23D:
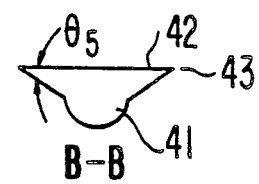

As shown in FIGS. 23C and 23D, the gates 42 are formed so that the restriction angle $\theta_5$ of the gate 42 near to the extremity of the runner 41 is greater than the restriction angle $\theta_1$ of the gate 42 farther from the extremity of the runner 41 so as to equalize the sums of each of the pressure losses in a portion of the runner 42 reaching each cavity and in the gate 42 for the same cavity. If, for some practical reasons, there are restrictive conditions of the restriction angles $\theta_1$, $\theta_2$, the pressure loss in the gate 42 may be adjusted by changing a width and/or depth of a gate outlet 43 of the respective gates 42.

Figure 24A:
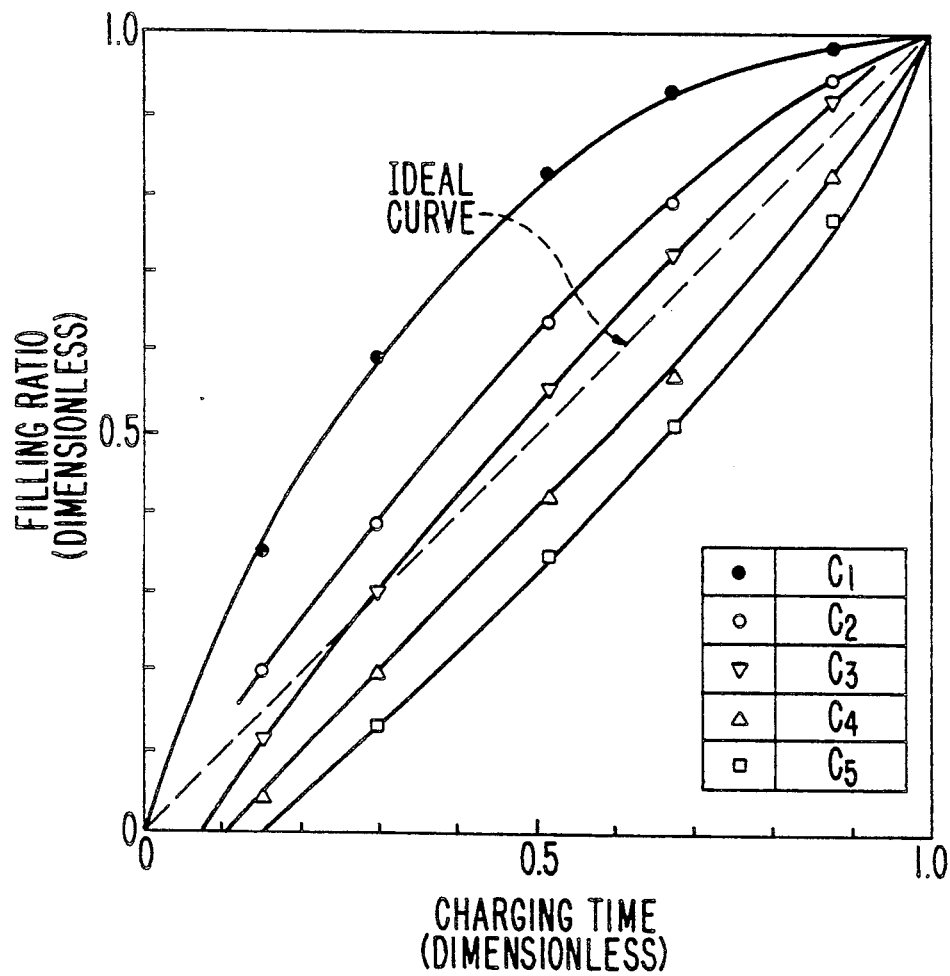
FIG. 24A is a graphical illustration of a relationship between charging time and filling ratio of a metal mold in accordance with a conventional method.
Figure 24B:
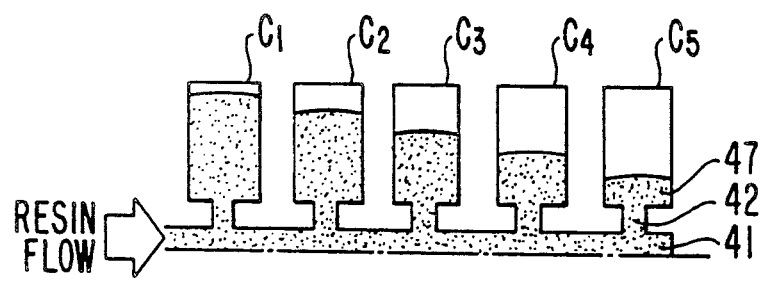
FIG. 24B is a schematic view of a charging of cavities of a metal mold with a molding resin in accordance with a conventional method.

The advantageous effects of the present invention will become more apparent from the following description in connection with FIGS. 24A, 24B, 25A, 25B, 26, and 27, with FIGS. 24A and 24B graphically and schematically explaining the process of filling cavities $C_1$, $C_2$, $C_3$, $C_4$, $C_5$ of a metal mold having a construction similar to that shown in FIGS. 23A and 23B and constructed without simulation by a conventional approach or method of processing the thermosetting resin 47. As shown in FIG. 24A, a dimensionless filling ratio is measureable along the ordinate, with a dimensionless filling time, namely, a time elapsed from a start of flow of the thermosetting resin 47 into a respective cavity $C_1$, $C_2$, $C_3$, $C_4$, $C_5$ being measureable along the abscissa. The dotted line in FIG. 24A represents an ideal filling mode in which the cavities $C_1$–$C_5$ are charged simultaneously with the thermosetting resin 47 at equal charging rates.

FIG. 24B illustrates a state of the cavities $C_1$–$C_5$ at a time 0.5 in FIG. 24A and, as evident from FIGS. 24A and 24B, the actual filling mode deviates greatly from the ideal filling mode curve shown in FIG. 24A, and the charging rate for the upper cavities $C_1$–$C_3$ is greater than the charging rate for the lower cavities $C_4$, $C_5$.

Figure 25A:
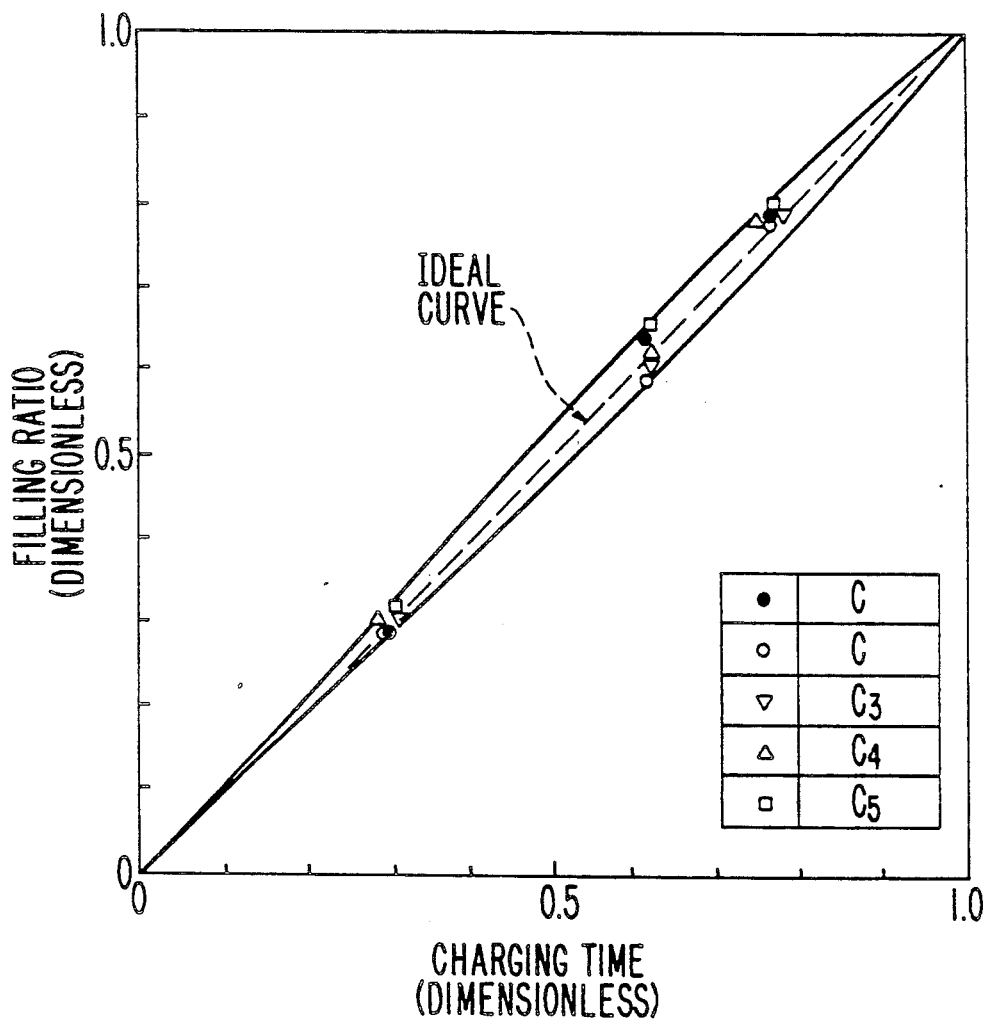
FIG. 25A is a graphical illustration of a relationship between charging time and filling ratio of a metal mold in accordance with the present invention.
Figure 25B:
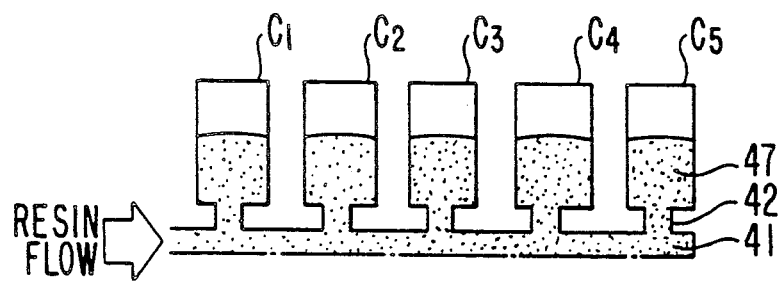
FIG. 25B is a schematic view of a mode of charging cavities of a metal mold in accordance with the present invention.

FIGS. 25A and 25B graphically and schematically illustrate the process of filling the cavities $C_1$, $C_2$, $C_3$, $C_4$, $C_5$ of a metal mold in accordance with the design method of the present invention on the basis of data obtained through the simulation of flow of the thermosetting resin 47 with a particular thermosetting resin.

FIG. 25B represents the state of the cavities $C_1$, $C_5$ at a time of 0.5 in FIG. 25A. As evident from FIGS. 25A and 25B all of the cavities $C_1$–$C_5$ are charged with the thermosetting resin 47 in filling modes very close to the ideal filling mode represented by the ideal curve in FIG. 25A and at substantially equal charging rates.

Figure 26:
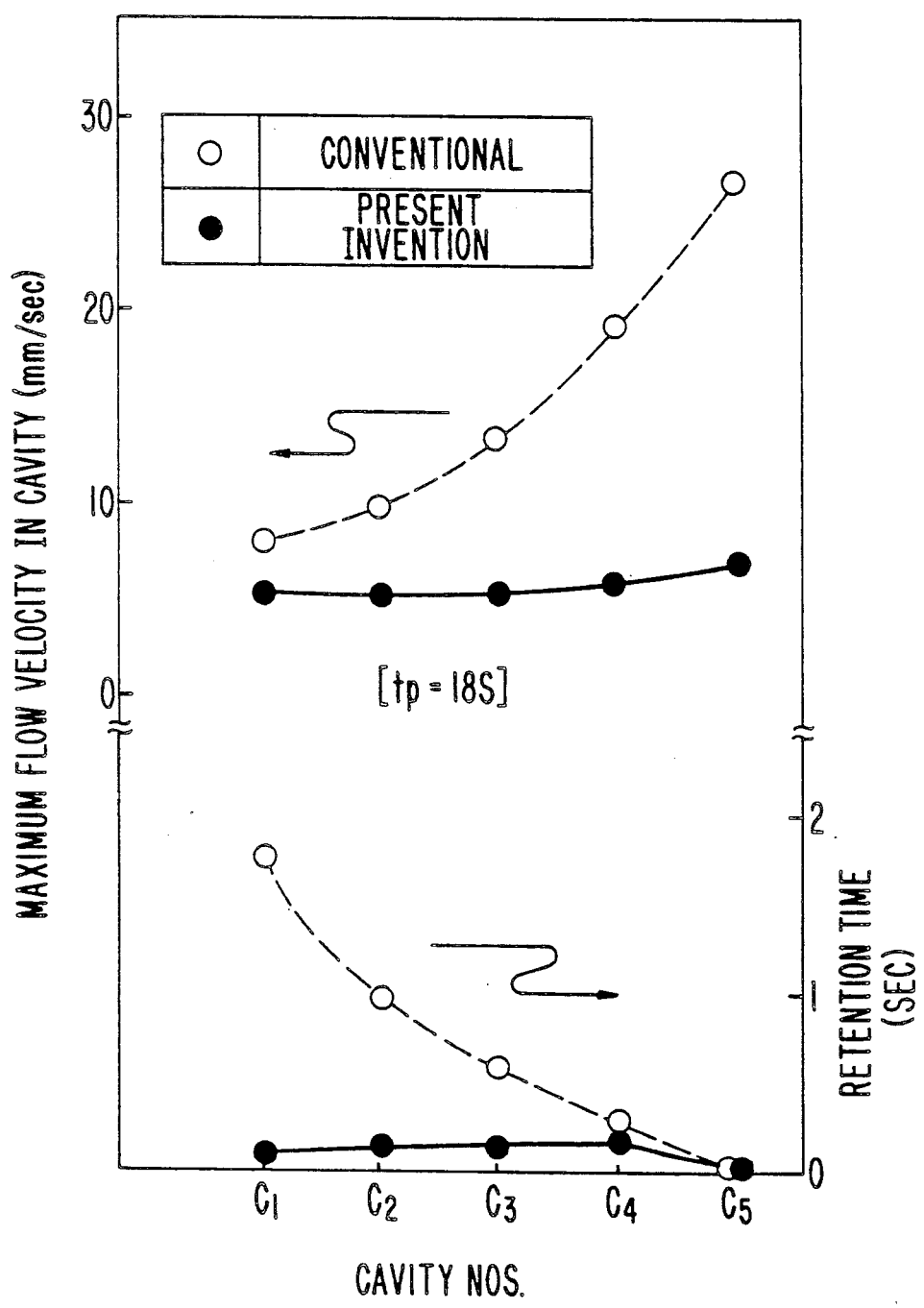
FIG. 26 is a graphical illustration of a maximum flow velocity of a molding resin in cavities and retention time for the cavities.

FIG. 26 provides a graphical illustration of a maximum flow velocity of the thermosetting resin 47 in each cavity $C_1$–$C_5$, and resin retention time, namely, a time period between a completion of the filling of the respective cavities $C_1$–$C_5$ with the thermosetting resin 47 and a completion of the injection operation of the plunger 49. In FIG. 26, the resin injection time is represented by $t_p$. In a metal mold designed in accordance with conventional design techniques, the flow velocity is greater for the lower cavities than for the upper cavities due to the increase in the flow rate for the lower cavities every time the upper cavity is filled with the thermosetting resin and the retention time is greater for the upper cavities are charged with the thermosetting resin 47 in the manner shown in FIGS. 24A and 24B. On the other hand, in the metal mold constructed in accordance with the present invention, flow velocities in the cavities $C_1$–$C_5$ are substantially the same and the retention time is almost zero for all of the cavities $C_1$–$C_5$ because the cavities $C_1$–$C_5$ are charged with the thermosetting resin 47 at equal charging rates as shown in FIGS. 25A and 25B.

Figure 27:
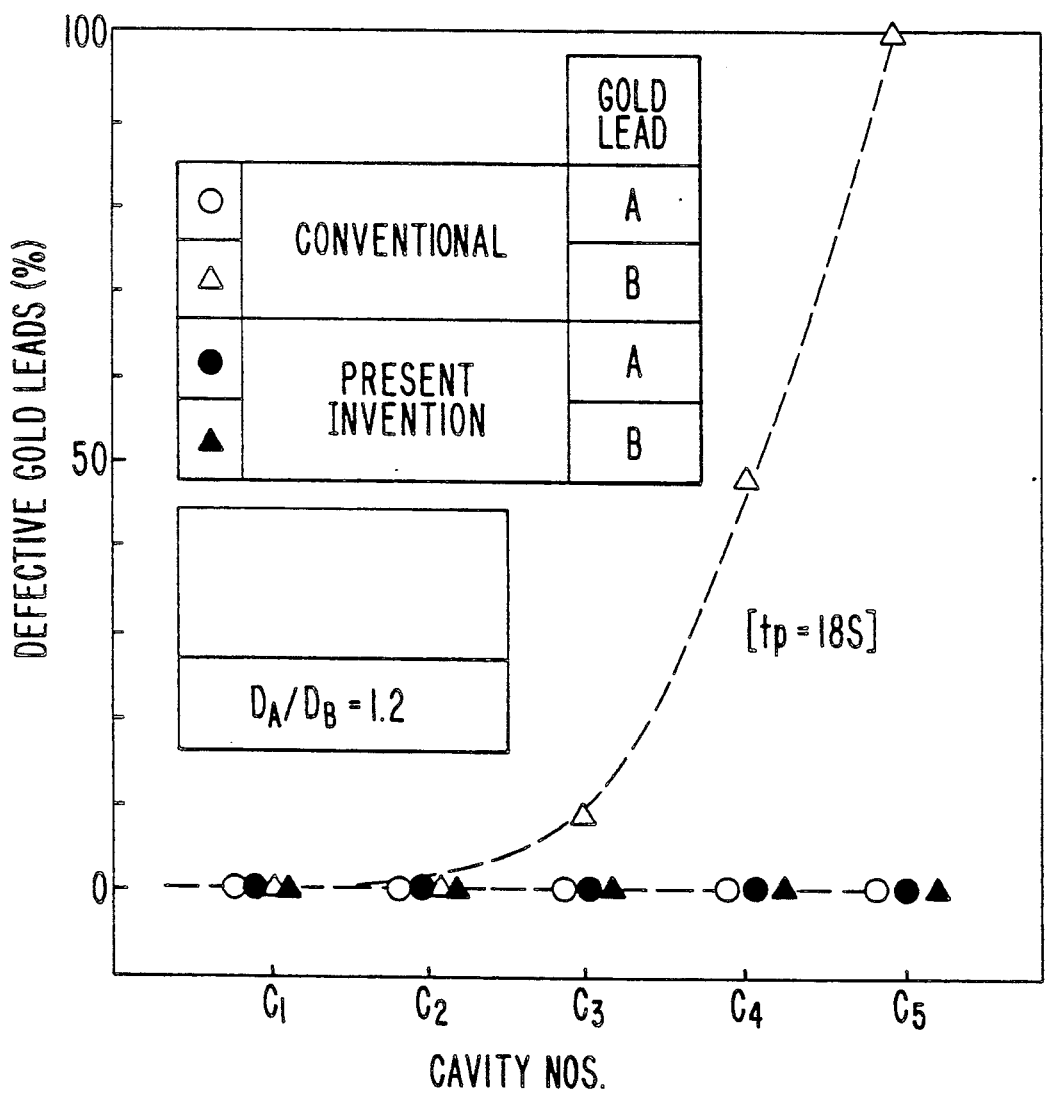
FIG. 27 is a graphical illustration of a defect percent of gold leaves in terms of distortion of the gold leaves.

FIG. 27 provides a graphical illustration of the percent defects of resin-filled devices in terms of gold lead distortion. In FIG. 27 a diameter $D_A$ of the gold leads A is greater than the diameter $D_B$ of the gold leads B. None of the gold leads A of the device is sealed with the resin using the metal mold constructed by conventional techniques and the device is sealed with a resin utilizing a metal mold designed and constructed in accordance with the present invention are distorted. The percent defective of the gold leads B of devices sealed with the resin by utilizing a metal mold designed by a conventional design method is greater for devices resin-sealed in lower cavities, which indicates that the distortion of the thin gold leads B increases with the increase in flow of the velocity of the resin. Since the flow velocities of the resin in all of the cavities of the metal mold constructed in accordance with the present invention are the same and constant, even the thin gold leads B are not distorted.

Table 3 summarizes the percent defective in terms of external appearance of resin-sealed devices comparing conventional design methods and the method contemplated by the present invention.

TABLE 3

| Design method | Percent defective (%) | |
| --- | --- | --- |
| | $t_p$ = 18 sec | $t_p$ = 30 sec |
| Conventional | 0 | 100 |
| The present invention | 0 | 0 |

As shown in Table 3, when $t_p$=18 sec, any resin-sealed devices having a faulty appearance do not occur regardless of the design method of the metal mold. However, when $t_p$=30 sec, the percent defective of the resin-sealed devices using the metal mold constructed in accordance with conventional techniques is 100% which is due to an excessively long retention time allowing the thermosetting resin to harden before a sufficient pressure is applied to the cavities. In contradistinction to the metal mold designed in accordance with conventional techniques, as apparent from Table 3, no resin-sealed device sealed with a resin by using a metal mold constructed by the present invention is defective because the retention time is substantially zero.

By virtue of the above-noted features of the present invention described hereinabove, optimum values for the dimensions of a runner of a metal mold for mass production and optimum molding conditions can be quickly and highly accurately determined through theoretical analysis. Accordingly, the time period required for a development of new products is considerably reduced by virtue of the fact that trial fabrication of metal molds can be omitted and defective molding is reduced, with the cost of the resin-sealed devices also being substantially reduced by virtue of the use of thinner gold leads.

While we have shown and described several embodiments in accordance with the present invention, it is understood that the same is not limited thereto but is susceptible to numerous changes and modifications as known to one of ordinary skill in the art, and we therefore do not wish to be limited to the details shown and described herein, but intend to cover all such modifications as are encompassed by the scope of the appended claims.

We claim:

1. A device for measuring a flow and curing characteristics of a resin, the device comprising a metal mold means including a pot means for accommodating the resin and a flow passage means connected to said pot means;

a plunger means for displacing resin from said pot means into said flow passage means;

pressure detector means provided in said metal mold means for detecting a pressure of the resin and providing an output signal of a detected pressure;

displacement detector means for detecting a position of said plunger means and providing an output signal of a detected position;

data processing means for storing and arranging the output signals received from said pressure detector means and said displacement detector means;

calculating means for converting signals processed by the data processing means into a physical quantity and calculating a combination of said physical quantity and at least one constant calculated from various dimensions of said flow passage means of said metal mold means; and outputting means for outputting a result of the calculation from said calculating means, wherein said metal mold means further includes a single runner having a first end connected to said pot means, said flow passage means includes a single flow passage connected to a second end of said runner opposite to said pot means, said single flow passage having uniform sectional dimensions transverse to a flow direction of the resin, sand wherein a cross-sectional area of said single flow passage is less than a cross-sectional area of said runner.

2. A device for measuring flow and curing characteristics of resin according to claim 1, wherein said cross-sectional area of said single flow passage of said metal mold means is substantially circular.

3. A device for measuring flow and curing characteristics of a resin according to claim 2, wherein said single flow passage of said metal mold has a spiral configuration as viewed in a flow direction of the resin.

4. A device for measuring flow and curing characteristics of a resin according to claim 1, wherein said pressure detector means is mounted on a wall of said runner of said metal mold means.

5. A device for measuring flow and curing characteristics of a resin according to claim 1, wherein said metal mold means is constructed such that the single flow passage is separable from the runner.

6. A device for measuring flow and curing characteristics of a resin, the device comprising a metal mold means including a pot means for accommodating the resin and a flow passage means connected to said pot means;

a plunger means for displacing resin from said pot means into said flow passage means;

pressure detector means provided in said metal mold means for detecting a pressure of the resin and providing an output signal of a detected pressure;

displacement detector means for detecting a position of said plunger means and providing an output signal of a detected position;

data processing means for storing and arranging the output signals received from said pressure detector means and said displacement detector means;

calculating means for converting signals processed by the data processing means into a physical quantity and calculating a combination of said physical quantity and at least one constant calculated from various dimensions of said flow passage means of said metal mold means; and outputting means for outputting a result of the calculation from said calculating means, wherein said metal mold means further includes a single runner having a first end connected to said pot means, said flow passage means includes a single flow passage connected to a second end of said runner opposite to said pot means, said single flow passage having uniform sectional dimensions transverse to a flow direction of the resin, and wherein a cross-sectional area of said single flow passage is less than a cross-sectional area of said runner, wherein said pressure detector means is adapted to sense at least a first and second pressure level and provide output signals thereof, and wherein when the output signal of said pressure detector means exceeds the first pressure level, the resin begins to flow into said flow passage means and when the output signal of sid pressure detector means exceeds the second pressure level the measurement is terminated.

7. A device for measuring flow and curing characteristics of a resin, the device comprising a metal mold means including a pot means for accommodating the resin and a flow passage means connected to said pot means;

a plunger means for displacing resin from said pot means into said flow passage means;

pressure detector means provided in said metal mold means for detecting a pressure of the resin and providing an output signal of a detected pressure;

displacement detector means for detecting a position of said plunger means and providing an output signal of a detected position;

data processing means for storing and arranging the output signal received from said pressure detector means and said displacement detector means;

calculating means for converting signals processed by the data processing means into a physical quantity and calculating a combination of said physical quantity and at least one constant calculated from various dimensions of said flow passage means of said metal mold means; and outputting means for outputting a result of the calculation from said calculating means, wherein said metal mold means further includes a single runner having a first end connected to said pot means, said flow passage means includes a single flow passage connected to a second end of said runner opposite to said pot means, said single flow passage having uniform sectional dimensions transverse to a flow direction of the resin, wherein a cross-sectional area of said single flow passage is less than a cross-sectional area of said runner, and wherein said pressure detector means is adapted to sense at least a first and second pressure level and provide output signals thereof, wherein when the output signal of said pressure detector means exceeds the first pressure level, the resin begins to flow into said flow passage means and when the output signal of said pressure detector means exceeds the second pressure level the measurement is terminated, and, wherein said calculating means is adapted to calculate a difference between adjacent output signals at said displacement detector means and, when a difference is less than a predetermined level and the output signal of the pressure detector means exceeds the second pressure level, the measurement is terminated.

8. A device for measuring flow and curing characteristics of a resin, the device comprising a metal mold means including a pot means for accommodating the resin and a flow passage means connected to said pot means;

a plunger means for displacing resin from said pot means into said flow passage means;

pressure detector means provided in said metal mold means for detecting a pressure of the resin and providing an output signal of a detected pressure;

displacement detector means for detecting a position of said plunger means and providing an output signal of a detected position;

data processing means for storing and arranging the output signals received from said pressure detector means and said displacement detector means;

calculating means for converting signals processed by the data processing means into a physical quantity and calculating a combination of said physical quantity and at least one constant calculated from various dimensions of said flow passage means of said metal mold means; and outputting means for outputting a result of the calculation from said calculating means, wherein said metal mold means further includes a single runner having a first end connected to said pot means, said flow passage means includes a single flow passage connected to a second end of said runner opposite to said pot means, said single flow passage having uniform sectional dimensions transverse to a flow direction of the resin, and wherein a cross-sectional area of said single flow passage is less than a cross-sectional area of said runner, wherein said pressure detector means is adapted to sense at least a first and second pressure level and provide output signals thereof, wherein when the output signal of said pressure detector means exceeds the first pressure level, the resin begins to flow into said flow passage means and when the output signal of said pressure detector means exceeds the second pressure level the measurement is terminated and, wherein a changing rate of pressure data relative to a time period is retroactively determined from a point of time at which the measurement terminates, and wherein a point of time at which a value of the changing rate of pressure data becomes less than a predetermined value is a resin flow stopping point of time.

9. An apparatus for measuring flow and curing characteristics of a thermosetting resin, the apparatus comprising:

a mold means having a pot means for accommodating the thermosetting resin, a runner means connected to said pot means, and a circular pipe flow passage means connected to said runner means, said circular pipe flow passage means having a smaller cross-sectional area than a cross-sectional area of said runner means;

a pressure detector means for detecting a pressure of the thermosetting resin flow into the circular pipe flow passage means from said runner means;

a plunger means for feeding the resin from said pot means into said mold means;

a displacement detector means for detecting a displacement of said plunger means;

data processing means for inputting a signal from said pressure detector means and a signal from said displacement detector means and calculating an average apparent viscosity in dependance upon predetermined values of said mold means and signals from said displacement detector means and said pressure detector means.

10. A metal mold comprising a pot means for accommodating a thermosetting resin, a runner means having a first end connected to said pot means for receiving the thermosetting resin from the pot means, a single flow passage means connected to said runner means for receiving the thermosetting resin from said runner means, said flow passage means having a uniform circular cross-sectional configuration and extending along a spiral path, and wherein a cross-sectional area of said flow passage means is less than a cross-sectional area of said runner means.

11. A device for measuring flow and curing characteristics of a resin, the device comprising a metal mold means including a pot means for accommodating the resin and a flow passage means connected to said pot means;

a plunger means for displacing resin from said pot means into said flow passage means;

pressure detector means provided in said metal mold means for detecting a pressure of the resin and providing an output signal of a detected pressure;

displacement detector means for detecting a position of said plunger means and providing an output signal of a detected position;

data processing means for storing and arranging the output signals received from said pressure detector means and said displacement detector means;

calculating means for converting signals processed by the data processing means into a physical quantity and calculating a combination of said physical quantity and at least one constant calculated from various dimensions of said flow passage means of said metal mold means; and outputting means for outputting a result of the calculation from said calculating means, wherein said metal mold means further includes a single runner having a first end connected to said pot means, said flow passage means includes a single flow passage connected to a second end of said runner opposite to said pot means, said single flow passage having uniform sectional dimensions transverse to a flow direction of the resin, wherein a cross-sectional area of said single flow passage is less than a cross-sectional area of said runner, wherein said pressure detector means is mounted on a wall of said runner of said metal mold means, wherein said pressure detector means is adapted to sense at least a first and second pressure level and provide output signals thereof, and wherein when the output signal of said pressure detector means exceeds the first pressure level, the resin begins to flow into said flow passage means and when the output signal of said pressure detector means exceeds the second pressure level the measurement is terminated.

12. A device for measuring flow and curing characteristics of a resin, the device comprising a metal mold means including a pot means for accommodating the resin and a flow passage means connected to said pot means;

a plunger means for displacing resin from said pot means into said flow passage means;

pressure detector means provided in said metal mold means for detecting a pressure of the resin and providing an output signal of a detected pressure;

displacement detector means for detecting a position of said plunger means and providing an output signal of a detected position;

data processing means for storing and arranging the output signals received from said pressure detector means and said displacement detector means;

calculating means for converting signals processed by the data processing means into a physical quantity and calculating a combination of said physical quantity and at least one constant calculated from various dimensions of said flow passage means of said metal mold means; and outputting means for outputting a result of the calculation from said calculating means, wherein said metal mold means further includes a single runner having a first end connected to said pot means, said flow passage means includes a single flow passage connected to a second end of said runner opposite to said pot means, said single flow passage having uniform sectional dimensions transverse to a flow direction of the resin, wherein a cross-sectional area of said single flow passage is less than a cross-sectional area of said runner, wherein said pressure detector means is mounted on a wall of said runner of said metal mold means, and wherein said pressure detector means is adapted to sense at least a first and second pressure level and provide output signals thereof, wherein when the output signal of said pressure detector means exceeds the first pressure level, the resin begins to flow into said flow passage means and when the output signal of said pressure detector means exceeds the second pressure level the measurement is terminated, and, wherein said calculating means is adapted to calculate a difference between adjacent output signals at said displacement detector means and, when a difference is less than a predetermined level and the output signal of the pressure detector means exceeds the second pressure level, the measurement is terminated.

13. A device for measuring flow and curing characteristics of a resin, the device comprising a metal mold means including a pot means for accommodating the resin and a flow passage means connected to said pot means;

a plunger means for displacing resin from said pot means into said flow passage means;

pressure detector means provided in said metal mold means for detecting a pressure of the resin and providing an output signal of a detected pressure;

displacement detector means for detecting a position of said plunger means and providing an output signal of a detected position;

data processing means for storing and arranging the output signals received from said pressure detector means and said displacement detector means;

calculating means for converting signals processed by the data processing means into a physical quantity and calculating a combination of said physical quantity and at least one constant calculated from various dimensions of said flow passage means of said metal mold means; and outputting means for outputting a result of the calculation from said calculating means, wherein said metal mold means further includes a single runner having a first end connected to said pot means, said flow passage means includes a single flow passage connected to a second end of said runner opposite to said pot means, said single flow passage having uniform sectional dimensions transverse to a flow direction of the resin, and wherein a cross-sectional area of said single flow passage is less than a cross-sectional area of said runner, wherein said pressure detector means is mounted on a wall of said runner of said metal mold means, wherein said pressure detector means is adapted to sense at least a first and second pressure level and provide output signals thereof, and wherein when the output signal of said pressure detector means exceeds the first pressure level, the resin begins to flow into said flow passage means and when the output signal of said pressure detector means exceeds the second pressure level the measurement is terminated, wherein a changing rate of pressure data relative to a time period is retroactively determined form a point of time at which the measurement terminates, and wherein a point of time at which a value of the changing rate of pressure data becomes less than a predetermined value is a resin flow stopping point of time.

* * * * *